US011664637B2

(12) United States Patent
Sierra et al.

(10) Patent No.: US 11,664,637 B2
(45) Date of Patent: *May 30, 2023

(54) PICOSECOND LASER APPARATUS AND METHODS FOR TREATING TARGET TISSUES WITH SAME

(71) Applicant: CYNOSURE, LLC, Westford, MA (US)

(72) Inventors: Rafael Armando Sierra, Palmer, MA (US); Mirko Georgiev Mirkov, Chelmsford, MA (US)

(73) Assignee: CYNOSURE, LLC, Westford, MA (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/395,081

(22) Filed: Aug. 5, 2021

(65) Prior Publication Data

US 2021/0367395 A1 Nov. 25, 2021

Related U.S. Application Data

(63) Continuation of application No. 16/784,797, filed on Feb. 7, 2020, now Pat. No. 11,095,087, which is a continuation of application No. 16/363,597, filed on Mar. 25, 2019, now Pat. No. 10,581,217, which is a continuation of application No. 15/721,714, filed on Sep. 29, 2017, now Pat. No. 10,305,244, which is a continuation of application No. 14/394,960, filed as application No. PCT/US2013/032228 on Mar. 15, 2013, now Pat. No. 9,780,518.

(60) Provisional application No. 61/625,961, filed on Apr. 18, 2012.

(51) Int. Cl.
| | | |
|---|---|---|
| H01S 3/30 | (2006.01) | |
| H01S 3/094 | (2006.01) | |
| H01S 3/102 | (2006.01) | |
| H01S 3/1106 | (2023.01) | |
| H01S 3/08 | (2023.01) | |
| H01S 3/1109 | (2023.01) | |
| H01S 3/16 | (2006.01) | |
| H01S 3/107 | (2006.01) | |
| A61B 18/00 | (2006.01) | |
| H01S 3/11 | (2023.01) | |

(52) U.S. Cl.
CPC .... *H01S 3/094076* (2013.01); *H01S 3/08054* (2013.01); *H01S 3/1024* (2013.01); *H01S 3/1106* (2013.01); *H01S 3/1109* (2013.01); *H01S 3/1611* (2013.01); *H01S 3/1673* (2013.01); *A61B 2018/00458* (2013.01); *F04C 2270/0421* (2013.01); *H01S 3/094038* (2013.01); *H01S 3/107* (2013.01); *H01S 3/1075* (2013.01); *H01S 3/1103* (2013.01); *H01S 3/1618* (2013.01); *H01S 3/1623* (2013.01); *H01S 3/1643* (2013.01)

(58) Field of Classification Search
CPC .......... H01S 3/094076; H01S 3/08054; H01S 3/1024; H01S 3/1106; H01S 3/1109; H01S 3/1611; H01S 3/1673; H01S 3/107; H01S 3/1075; H01S 3/1103; H01S 3/1618; H01S 3/1623; H01S 3/1643; H01S 3/0627
See application file for complete search history.

(56) References Cited

U.S. PATENT DOCUMENTS

| | | |
|---|---|---|
| 853,033 A | 5/1907 | Roberts |
| 1,590,283 A | 6/1926 | Catlin |
| 1,676,183 A | 7/1928 | Garfunkle |
| 1,706,161 A | 3/1929 | Hollnagen |
| 2,068,721 A | 1/1937 | Wappler et al. |
| 2,472,385 A | 6/1949 | Rollman |
| 2,669,771 A | 2/1954 | Burge et al. |
| 3,243,650 A | 3/1966 | Hawkins et al. |
| 3,261,978 A | 7/1966 | Brenman |
| 3,284,665 A | 11/1966 | Goncz |
| 3,327,712 A | 6/1967 | Kaufmann |
| 3,465,203 A | 9/1969 | Michaels et al. |
| 3,486,070 A | 12/1969 | Engel |
| 3,524,144 A | 8/1970 | Buser et al. |
| 3,527,932 A | 9/1970 | Thomas |

(Continued)

FOREIGN PATENT DOCUMENTS

| | | |
|---|---|---|
| AT | 400305 | 4/1995 |
| AU | 1851583 | 3/1984 |

(Continued)

OTHER PUBLICATIONS

US 6,230,044 B1, 05/2001, Afanassieva et al. (withdrawn)
[No Author] Bioptron Light Therapy System. Website print-out, accessed Jul. 13, 2006 (2 pages).
[No Author] Derma Chiller advertisement (2 pages) from Paradigm Trex.
[No Author] IPG Data Sheet for TFL Thulium Laser, Jun. 2001.

(Continued)

*Primary Examiner* — Kinam Park
(74) *Attorney, Agent, or Firm* — K&L Gates LLP

(57) ABSTRACT

Apparatuses and methods are disclosed for applying laser energy having desired pulse characteristics, including a sufficiently short duration and/or a sufficiently high energy for the photomechanical treatment of skin pigmentations and pigmented lesions, both naturally-occurring (e.g., birthmarks), as well as artificial (e.g., tattoos). The laser energy may be generated with an apparatus having a resonator with the capability of switching between a modelocked pulse operating mode and an amplification operating mode. The operating modes are carried out through the application of a time-dependent bias voltage, having waveforms as described herein, to an electro-optical device positioned along the optical axis of the resonator.

32 Claims, No Drawings

(56) References Cited

U.S. PATENT DOCUMENTS

| | | |
|---|---|---|
| 3,538,919 A | 11/1970 | Meyer |
| 3,597,652 A | 8/1971 | Gates, Jr. |
| 3,622,743 A | 11/1971 | Muncheryan |
| 3,651,425 A | 3/1972 | McKnight |
| 3,653,778 A | 4/1972 | Freiling |
| 3,667,454 A | 6/1972 | Prince |
| 3,693,623 A | 9/1972 | Harte et al. |
| 3,699,967 A | 10/1972 | Anderson |
| 3,725,733 A | 4/1973 | Mack et al. |
| 3,766,393 A | 10/1973 | Herzog et al. |
| 3,766,488 A | 10/1973 | Kohn |
| 3,769,963 A | 11/1973 | Goldman et al. |
| 3,793,723 A | 2/1974 | Kuris et al. |
| 3,794,028 A | 2/1974 | Mueller et al. |
| 3,815,046 A | 6/1974 | Johnson et al. |
| 3,818,373 A | 6/1974 | Chun et al. |
| 3,818,914 A | 6/1974 | Bender |
| 3,821,510 A | 6/1974 | Muncheryan |
| 3,834,391 A | 9/1974 | Block |
| 3,843,865 A | 10/1974 | Nath |
| 3,846,811 A | 11/1974 | Nakamura et al. |
| 3,857,015 A | 12/1974 | Clark et al. |
| 3,858,577 A | 1/1975 | Bass et al. |
| 3,861,921 A | 1/1975 | Hoffmann et al. |
| 3,885,569 A | 5/1975 | Judson |
| 3,890,537 A | 6/1975 | Park et al. |
| 3,900,034 A | 8/1975 | Katz et al. |
| 3,909,649 A | 9/1975 | Arsena |
| 3,914,709 A | 10/1975 | Pike et al. |
| 3,939,560 A | 2/1976 | Lyall |
| 3,977,083 A | 8/1976 | Leslie et al. |
| 3,980,861 A | 9/1976 | Fukunaga |
| 4,019,156 A | 4/1977 | Fountain et al. |
| 4,037,136 A | 7/1977 | Hoene |
| 4,038,984 A | 8/1977 | Sittner |
| 4,047,106 A | 9/1977 | Robinson |
| 4,065,370 A | 12/1977 | Noble et al. |
| 4,122,853 A | 10/1978 | Smith |
| 4,133,503 A | 1/1979 | Bliss |
| 4,139,342 A | 2/1979 | Sheldrake et al. |
| 4,154,240 A | 5/1979 | Ikuno et al. |
| 4,176,324 A | 11/1979 | Aldag et al. |
| 4,188,927 A | 2/1980 | Harris |
| 4,213,462 A | 2/1980 | Sato |
| 4,228,800 A | 10/1980 | Degler, Jr. et al. |
| 4,233,493 A | 11/1980 | Nath et al. |
| 4,254,333 A | 3/1981 | Bergstrom |
| 4,259,123 A | 3/1981 | Tymkewicz |
| 4,269,067 A | 5/1981 | Tynan et al. |
| 4,273,109 A | 6/1981 | Enderby |
| 4,275,335 A | 6/1981 | Ishida et al. |
| 4,291,281 A | 9/1981 | Pinard et al. |
| 4,292,601 A | 9/1981 | Aldag et al. |
| 4,293,827 A | 10/1981 | McAllister et al. |
| 4,298,005 A | 11/1981 | Mutzhas |
| 4,299,912 A | 11/1981 | Shiba et al. |
| 4,302,730 A | 11/1981 | Jernigan |
| 4,313,431 A | 2/1982 | Frank |
| 4,316,467 A | 2/1982 | Muckerheide |
| 4,333,197 A | 6/1982 | Kuris |
| 4,335,726 A | 6/1982 | Kolstedt |
| 4,336,809 A | 6/1982 | Clark |
| 4,364,015 A | 12/1982 | Drake et al. |
| 4,375,684 A | 5/1983 | Everett |
| 4,388,924 A | 6/1983 | Weissman et al. |
| 4,409,479 A | 10/1983 | Sprague et al. |
| 4,428,368 A | 1/1984 | Torii |
| 4,435,808 A | 3/1984 | Javan |
| 4,445,217 A | 4/1984 | Acharekar et al. |
| 4,452,081 A | 6/1984 | Seppi |
| 4,456,872 A | 6/1984 | Froeschle |
| 4,461,294 A | 7/1984 | Baron |
| 4,488,104 A | 12/1984 | Suzuki |
| 4,489,415 A | 12/1984 | Jones et al. |
| 4,492,601 A | 1/1985 | Nakasone et al. |
| 4,503,854 A | 3/1985 | Jako |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A | 9/1985 | Nath et al. |
| 4,553,546 A | 11/1985 | Javelle |
| 4,555,786 A | 11/1985 | Byer |
| 4,556,979 A | 12/1985 | Scott et al. |
| 4,559,943 A | 12/1985 | Bowers |
| 4,561,440 A | 12/1985 | Kubo et al. |
| 4,566,271 A | 1/1986 | French et al. |
| 4,566,438 A | 1/1986 | Liese et al. |
| 4,569,345 A | 2/1986 | Manes |
| 4,576,177 A | 3/1986 | Webster, Jr. |
| 4,587,968 A | 5/1986 | Price |
| 4,591,762 A | 5/1986 | Nakamura |
| 4,592,353 A | 6/1986 | Daikuzono |
| 4,601,037 A | 7/1986 | McDonald |
| 4,601,753 A | 7/1986 | Soileau et al. |
| 4,608,978 A | 9/1986 | Rohr |
| 4,608,979 A | 9/1986 | Breidenthal et al. |
| 4,617,926 A | 10/1986 | Sutton |
| 4,623,929 A | 11/1986 | Johnson et al. |
| 4,629,884 A | 12/1986 | Bergstrom |
| 4,638,800 A | 1/1987 | Michel |
| 4,653,495 A | 3/1987 | Nanaumi |
| 4,656,641 A | 4/1987 | Scifres et al. |
| 4,662,368 A | 5/1987 | Hussein et al. |
| 4,677,347 A | 6/1987 | Nakamura |
| 4,686,986 A | 8/1987 | Fenyo et al. |
| 4,693,244 A | 9/1987 | Daikuzono |
| 4,693,556 A | 9/1987 | McCaughan, Jr. |
| 4,695,697 A | 9/1987 | Kosa |
| 4,710,677 A | 12/1987 | Halberstadt et al. |
| 4,718,416 A | 1/1988 | Nanaumi |
| 4,724,835 A | 2/1988 | Liss et al. |
| 4,733,660 A | 3/1988 | Itzkan |
| 4,735,201 A | 4/1988 | O'Reilly |
| 4,736,743 A | 4/1988 | Daikuzono |
| 4,736,745 A | 4/1988 | Gluckman |
| 4,740,047 A | 4/1988 | Abe et al. |
| 4,741,338 A | 5/1988 | Miyamae |
| 4,745,909 A | 5/1988 | Pelton et al. |
| 4,747,660 A | 5/1988 | Nishioka et al. |
| 4,749,913 A | 6/1988 | Stuermer et al. |
| 4,759,349 A | 7/1988 | Betz et al. |
| 4,773,413 A | 9/1988 | Hussein et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,813,412 A | 3/1989 | Yamazaki et al. |
| 4,813,762 A | 3/1989 | Leger et al. |
| 4,819,669 A | 4/1989 | Politzer |
| 4,826,431 A | 5/1989 | Fujimura et al. |
| 4,829,262 A | 5/1989 | Furumoto |
| 4,832,024 A | 5/1989 | Boussignac et al. |
| 4,840,174 A | 6/1989 | Gluckman |
| 4,840,563 A | 6/1989 | Altendorf |
| 4,845,608 A | 7/1989 | Gdula |
| 4,848,339 A | 7/1989 | Rink et al. |
| 4,852,107 A | 7/1989 | Hamal et al. |
| 4,852,549 A | 8/1989 | Mori |
| 4,860,172 A | 8/1989 | Schlager et al. |
| 4,860,303 A | 8/1989 | Russell |
| 4,860,743 A | 8/1989 | Abela |
| 4,860,744 A | 8/1989 | Johnson et al. |
| 4,862,886 A | 9/1989 | Clarke et al. |
| 4,862,888 A | 9/1989 | Yessik |
| 4,862,903 A | 9/1989 | Campbell |
| 4,871,479 A | 10/1989 | Bachelard et al. |
| 4,878,224 A | 10/1989 | Kuder |
| 4,884,560 A | 12/1989 | Kuracina |
| 4,887,600 A | 12/1989 | Watson et al. |
| 4,889,525 A | 12/1989 | Yuhas et al. |
| 4,890,898 A | 1/1990 | Bentley et al. |
| 4,891,817 A | 1/1990 | Duarte |
| 4,896,329 A | 1/1990 | Knaak |
| 4,898,438 A | 2/1990 | Mori |

(56) References Cited

U.S. PATENT DOCUMENTS

| | | |
|---|---|---|
| 4,898,439 A | 2/1990 | Mori |
| 4,901,323 A | 2/1990 | Hawkins et al. |
| 4,905,690 A | 3/1990 | Ohshiro et al. |
| 4,910,438 A | 3/1990 | Farnsworth |
| 4,913,142 A | 4/1990 | Kittrell et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos |
| 4,931,053 A | 6/1990 | L'Esperance |
| 4,932,954 A | 6/1990 | Wondrazek et al. |
| 4,945,239 A | 7/1990 | Wist et al. |
| 4,950,266 A | 8/1990 | Sinofsky |
| 4,955,882 A | 9/1990 | Hakky |
| 4,968,314 A | 11/1990 | Michaels |
| 4,972,427 A | 11/1990 | Streifer et al. |
| 4,973,848 A | 11/1990 | Kolobanov et al. |
| 4,976,308 A | 12/1990 | Faghri |
| 4,976,709 A | 12/1990 | Sand |
| 4,977,571 A | 12/1990 | Furumoto et al. |
| 4,978,186 A | 12/1990 | Mori |
| 4,979,180 A | 12/1990 | Muncheryan |
| 4,992,256 A | 2/1991 | Skaggs et al. |
| 4,994,060 A | 2/1991 | Rink et al. |
| 5,000,752 A | 3/1991 | Hoskin et al. |
| 5,006,293 A | 4/1991 | Hartman et al. |
| 5,009,658 A | 4/1991 | Damgaard-Iversen |
| 5,011,483 A | 4/1991 | Sleister |
| 5,027,359 A | 6/1991 | Leger et al. |
| 5,030,090 A | 7/1991 | Maeda et al. |
| 5,032,178 A | 7/1991 | Cornell |
| 5,037,421 A | 8/1991 | Boutacoff et al. |
| 5,041,109 A | 8/1991 | Abela |
| 5,046,494 A | 9/1991 | Searfoss et al. |
| 5,050,597 A | 9/1991 | Daikuzono |
| 5,056,515 A | 10/1991 | Abel |
| 5,057,099 A | 10/1991 | Rink |
| 5,057,104 A | 10/1991 | Chess |
| 5,059,192 A | 10/1991 | Zaias |
| 5,061,266 A | 10/1991 | Hakky |
| 5,060,243 A | 11/1991 | Furumoto |
| 5,065,515 A | 11/1991 | Iderosa |
| 5,066,292 A | 11/1991 | Müller et al. |
| 5,066,293 A | 11/1991 | Furumoto |
| 5,071,416 A | 12/1991 | Heller et al. |
| 5,071,417 A | 12/1991 | Sinofsky |
| 5,080,660 A | 1/1992 | Buelna |
| 5,090,019 A | 2/1992 | Scheps |
| 5,092,865 A | 3/1992 | Rink |
| 5,099,231 A | 3/1992 | Sato |
| 5,102,410 A | 4/1992 | Dressel |
| 5,108,388 A | 4/1992 | Trokel |
| 5,109,387 A | 4/1992 | Garden et al. |
| 5,112,328 A | 5/1992 | Taboada et al. |
| 5,127,395 A | 7/1992 | Bontemps |
| 5,129,896 A | 7/1992 | Hasson |
| 5,129,897 A | 7/1992 | Daikuzono |
| 5,132,980 A | 7/1992 | Connors et al. |
| 5,133,102 A | 7/1992 | Sakuma |
| 5,137,530 A | 8/1992 | Sand |
| 5,140,608 A | 8/1992 | Karpol et al. |
| 5,140,984 A | 8/1992 | Dew et al. |
| 5,147,353 A | 9/1992 | Everett |
| 5,147,356 A | 9/1992 | Bhatta |
| 5,151,097 A | 9/1992 | Daikuzono |
| 5,159,601 A | 10/1992 | Huber |
| 5,160,194 A | 11/1992 | Feldman |
| 5,163,935 A | 11/1992 | Black et al. |
| 5,171,564 A | 12/1992 | Nathoo et al. |
| 5,178,617 A | 1/1993 | Kuizenga et al. |
| 5,180,378 A | 1/1993 | Kung et al. |
| 5,182,557 A | 1/1993 | Lang |
| 5,182,857 A | 2/1993 | Simon |
| 5,190,541 A | 3/1993 | Abele et al. |
| 5,191,883 A | 3/1993 | Lennox et al. |
| 5,192,278 A | 3/1993 | Hayes et al. |
| 5,196,004 A | 3/1993 | Sinofsky |
| 5,197,470 A | 3/1993 | Helfer et al. |
| 5,201,731 A | 4/1993 | Hakky |
| 5,193,526 A | 5/1993 | Daikuzono |
| 5,207,671 A | 5/1993 | Franken et al. |
| 5,207,672 A | 5/1993 | Roth et al. |
| 5,207,673 A | 5/1993 | Ebling et al. |
| 5,209,748 A | 5/1993 | Daikuzono |
| 5,213,092 A | 5/1993 | Uram |
| 5,217,455 A | 6/1993 | Tan |
| 5,219,347 A | 6/1993 | Negus et al. |
| 5,222,907 A | 6/1993 | Katabuchi et al. |
| 5,222,953 A | 6/1993 | Dowlatshaki |
| 5,225,926 A | 7/1993 | Cuomo et al. |
| 5,226,907 A | 7/1993 | Tankovich |
| 5,242,437 A | 9/1993 | Everett et al. |
| 5,242,438 A | 9/1993 | Saadatmanesh |
| 5,246,436 A | 9/1993 | Rowe |
| 5,249,192 A | 9/1993 | Kuizenga et al. |
| 5,254,114 A | 10/1993 | Reed, Jr. et al. |
| 5,255,277 A | 10/1993 | Carvalho |
| 5,257,970 A | 11/1993 | Dougherty |
| 5,257,991 A | 11/1993 | Fletcher et al. |
| 5,261,904 A | 11/1993 | Baker et al. |
| 5,267,399 A | 12/1993 | Johnston |
| 5,267,995 A | 12/1993 | Doiron et al. |
| 5,267,998 A | 12/1993 | Hagen |
| 5,269,777 A | 12/1993 | Doiron et al. |
| 5,269,780 A | 12/1993 | Roos |
| 5,281,211 A | 1/1994 | Parel et al. |
| 5,281,216 A | 1/1994 | Klicek |
| 5,282,797 A | 2/1994 | Chess |
| 5,284,154 A | 2/1994 | Raymond et al. |
| 5,287,372 A | 2/1994 | Ortiz |
| 5,287,380 A | 2/1994 | Hsia |
| 5,290,273 A | 3/1994 | Tan |
| 5,290,274 A | 3/1994 | Levy et al. |
| 5,292,320 A | 3/1994 | Brown et al. |
| 5,293,880 A | 3/1994 | Levitt |
| 5,300,063 A | 4/1994 | Tano et al. |
| 5,300,065 A | 4/1994 | Anderson |
| 5,300,097 A | 4/1994 | Lerner et al. |
| 5,303,585 A | 4/1994 | Lichte |
| 5,304,167 A | 4/1994 | Freiberg |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,307,369 A | 4/1994 | Kimberlin |
| 5,308,311 A | 5/1994 | Eggers et al. |
| 5,312,395 A | 5/1994 | Tan et al. |
| 5,312,396 A | 5/1994 | Feld et al. |
| 5,320,618 A | 6/1994 | Gustafsson |
| 5,320,620 A | 6/1994 | Long et al. |
| 5,330,470 A | 7/1994 | Hagen |
| 5,331,649 A | 7/1994 | Dacquay et al. |
| 5,334,191 A | 8/1994 | Poppas et al. |
| 5,334,193 A | 8/1994 | Nardella |
| 5,336,217 A | 8/1994 | Buys et al. |
| 5,336,221 A | 8/1994 | Anderson |
| 5,342,358 A | 8/1994 | Daikuzono et al. |
| 5,344,418 A | 9/1994 | Ghaffari |
| 5,344,434 A | 9/1994 | Talmore |
| 5,346,488 A | 9/1994 | Prince et al. |
| 5,348,551 A | 9/1994 | Spears et al. |
| 5,349,590 A | 9/1994 | Amirkhanian et al. |
| 5,350,376 A | 9/1994 | Brown |
| 5,353,020 A | 10/1994 | Schurmann |
| 5,353,790 A | 10/1994 | Jacques et al. |
| 5,354,294 A | 10/1994 | Chou |
| 5,356,081 A | 10/1994 | Sellar |
| 5,358,503 A | 10/1994 | Bertwell et al. |
| 5,360,426 A | 11/1994 | Muller et al. |
| 5,366,456 A | 11/1994 | Rink et al. |
| 5,368,031 A | 11/1994 | Cline et al. |
| 5,368,038 A | 11/1994 | Fraden |
| 5,369,496 A | 11/1994 | Alfano et al. |

(56) References Cited

U.S. PATENT DOCUMENTS

| | | |
|---|---|---|
| 5,369,831 A | 12/1994 | Bock |
| 5,370,642 A | 12/1994 | Keller |
| 5,370,649 A | 12/1994 | Gardetto et al. |
| 5,380,317 A | 1/1995 | Everett et al. |
| 5,383,876 A | 1/1995 | Nardella |
| 5,386,427 A | 1/1995 | Zayhowski |
| 5,387,211 A | 2/1995 | Saadatmanesh |
| 5,395,356 A | 3/1995 | King et al. |
| 5,403,306 A | 4/1995 | Edwards et al. |
| 5,405,368 A | 4/1995 | Eckhouse |
| 5,409,446 A | 4/1995 | Rattner |
| 5,409,479 A | 4/1995 | Dew et al. |
| 5,409,481 A | 4/1995 | Poppas et al. |
| 5,415,654 A | 5/1995 | Daikuzono |
| 5,421,337 A | 6/1995 | Richards-Kortum |
| 5,421,339 A | 6/1995 | Ramanujam et al. |
| 5,422,112 A | 6/1995 | Williams |
| 5,423,800 A | 6/1995 | Ren et al. |
| 5,423,803 A | 6/1995 | Tankovich et al. |
| 5,423,805 A | 6/1995 | Brucker et al. |
| 5,425,728 A | 6/1995 | Tankovich |
| 5,425,735 A | 6/1995 | Rosen et al. |
| 5,425,754 A | 6/1995 | Braun et al. |
| 5,439,954 A | 8/1995 | Bush |
| 5,441,499 A | 8/1995 | Fritzsch |
| 5,445,608 A | 8/1995 | Chen et al. |
| 5,445,611 A | 8/1995 | Eppstein et al. |
| 5,454,807 A | 10/1995 | Lennox et al. |
| 5,456,682 A | 10/1995 | Edwards et al. |
| 5,458,140 A | 10/1995 | Eppstein et al. |
| 5,464,436 A | 11/1995 | Smith |
| 5,464,724 A | 11/1995 | Akiyama et al. |
| 5,470,331 A | 11/1995 | Daikuzono |
| 5,472,748 A | 12/1995 | Wolfe et al. |
| 5,474,549 A | 12/1995 | Ortiz et al. |
| 5,484,436 A | 1/1996 | Eggers et al. |
| 5,486,170 A | 1/1996 | Winston et al. |
| 5,486,172 A | 1/1996 | Chess |
| 5,488,626 A | 1/1996 | Heller et al. |
| 5,489,256 A | 2/1996 | Adair |
| 5,492,894 A | 2/1996 | Bascom et al. |
| 5,496,305 A | 3/1996 | Kittrell et al. |
| 5,496,307 A | 3/1996 | Daikuzono |
| 5,498,935 A | 3/1996 | McMahan et al. |
| 5,499,313 A | 3/1996 | Kleinerman |
| 5,501,680 A | 3/1996 | Kurtz et al. |
| 5,502,582 A | 3/1996 | Larson et al. |
| 5,505,726 A | 4/1996 | Meserol |
| 5,505,727 A | 4/1996 | Keller |
| 5,507,739 A | 4/1996 | Vassiliadis et al. |
| 5,519,534 A | 5/1996 | Smith et al. |
| 5,521,367 A | 5/1996 | Bard et al. |
| 5,522,813 A | 6/1996 | Trelles |
| 5,527,350 A | 6/1996 | Grove et al. |
| 5,527,368 A | 6/1996 | Supkis et al. |
| 5,530,711 A | 6/1996 | Scheps |
| 5,531,739 A | 7/1996 | Trelles |
| 5,531,740 A | 7/1996 | Black |
| 5,536,168 A | 7/1996 | Bourke |
| 5,540,676 A | 7/1996 | Freiberg |
| 5,540,678 A | 7/1996 | Long et al. |
| 5,540,681 A | 7/1996 | Strul et al. |
| 5,541,948 A | 7/1996 | Krupke et al. |
| 5,546,214 A | 8/1996 | Black et al. |
| 5,549,660 A | 8/1996 | Mendes et al. |
| 5,557,625 A | 9/1996 | Durville |
| 5,558,666 A | 9/1996 | Dewey et al. |
| 5,558,667 A | 9/1996 | Yarborough et al. |
| 5,561,881 A | 10/1996 | Klinger et al. |
| 5,571,098 A | 11/1996 | Domankevitz et al. |
| 5,578,029 A | 11/1996 | Trelles et al. |
| 5,578,866 A | 11/1996 | DePoorter et al. |
| 5,595,568 A | 1/1997 | Anderson et al. |
| 5,598,426 A | 1/1997 | Hsia et al. |
| 5,608,210 A | 3/1997 | Esparza et al. |
| 5,611,793 A | 3/1997 | Wilson et al. |
| 5,616,140 A | 4/1997 | Prescott |
| 5,618,284 A | 4/1997 | Sand |
| 5,620,478 A | 4/1997 | Eckhouse |
| 5,624,435 A | 4/1997 | Furumoto et al. |
| 5,626,631 A | 5/1997 | Eckhouse |
| 5,628,744 A | 5/1997 | Coleman et al. |
| 5,628,771 A | 5/1997 | Mizukawa et al. |
| 5,630,811 A | 5/1997 | Miller |
| 5,632,741 A | 5/1997 | Zavislan et al. |
| 5,634,711 A | 6/1997 | Kennedy et al. |
| 5,647,866 A | 7/1997 | Zaias et al. |
| 5,649,972 A | 7/1997 | Hochstein |
| 5,651,783 A | 7/1997 | Reynard |
| 5,652,481 A | 7/1997 | Johnson et al. |
| 5,653,706 A | 8/1997 | Zavislan et al. |
| 5,655,547 A | 8/1997 | Karni |
| 5,657,760 A | 8/1997 | Ying et al. |
| 5,658,148 A | 8/1997 | Neuberger et al. |
| 5,658,323 A | 8/1997 | Miller |
| 5,660,836 A | 8/1997 | Knowlton |
| 5,661,744 A | 8/1997 | Murakami et al. |
| 5,662,643 A | 9/1997 | Kung et al. |
| 5,662,644 A | 9/1997 | Swor |
| 5,668,824 A | 9/1997 | Furumoto |
| 5,671,315 A | 9/1997 | Tabuchi et al. |
| 5,673,451 A | 10/1997 | Moore et al. |
| 5,679,113 A | 10/1997 | Caisey et al. |
| 5,683,380 A | 11/1997 | Eckhouse et al. |
| 5,684,902 A | 11/1997 | Tada |
| 5,688,266 A | 11/1997 | Edwards et al. |
| 5,688,267 A | 11/1997 | Panescu et al. |
| 5,692,509 A | 12/1997 | Voss et al. |
| 5,698,866 A | 12/1997 | Doiron et al. |
| 5,707,369 A | 1/1998 | Vaitekunas et al. |
| 5,707,401 A | 1/1998 | Martin et al. |
| 5,707,403 A | 1/1998 | Grove et al. |
| 5,713,738 A | 2/1998 | Yarborough |
| 5,714,119 A | 2/1998 | Kawagoe et al. |
| 5,720,772 A | 2/1998 | Eckhouse |
| 5,722,397 A | 3/1998 | Eppstein |
| 5,725,522 A | 3/1998 | Sinofsky |
| 5,728,090 A | 3/1998 | Martin et al. |
| 5,735,844 A | 4/1998 | Anderson et al. |
| 5,735,884 A | 4/1998 | Thompson et al. |
| 5,738,678 A | 4/1998 | Patel |
| 5,742,392 A | 4/1998 | Anderson et al. |
| 5,743,901 A | 4/1998 | Grove et al. |
| 5,743,902 A | 4/1998 | Trost |
| 5,746,735 A | 5/1998 | Furumoto et al. |
| 5,748,822 A | 5/1998 | Miura et al. |
| 5,749,868 A | 5/1998 | Furumoto |
| 5,755,751 A | 5/1998 | Eckhouse |
| 5,759,162 A | 6/1998 | Oppelt et al. |
| 5,759,200 A | 6/1998 | Azar |
| 5,760,362 A | 6/1998 | Etoy |
| 5,769,076 A | 6/1998 | Maekawa et al. |
| 5,776,129 A | 7/1998 | Mersch |
| 5,782,249 A | 7/1998 | Weber et al. |
| 5,802,136 A | 9/1998 | Carol |
| 5,807,386 A | 9/1998 | Slatkine et al. |
| 5,810,801 A | 9/1998 | Anderson et al. |
| 5,810,802 A | 9/1998 | Panescu et al. |
| 5,812,567 A | 9/1998 | Jeon et al. |
| 5,813,855 A | 9/1998 | Crisio, Jr. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,818,580 A | 10/1998 | Murnick |
| 5,820,625 A | 10/1998 | Izawa et al. |
| 5,820,626 A | 10/1998 | Baumgardner |
| 5,822,034 A | 10/1998 | Shimashita et al. |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,830,209 A | 11/1998 | Savage et al. |
| 5,832,931 A | 11/1998 | Wachter et al. |

(56) References Cited

U.S. PATENT DOCUMENTS

| | | |
|---|---|---|
| 5,835,648 A | 11/1998 | Narciso, Jr. |
| 5,836,877 A | 11/1998 | Zavislan |
| 5,836,999 A | 11/1998 | Eckhouse et al. |
| 5,837,001 A | 11/1998 | Mackey |
| 5,840,048 A | 11/1998 | Cheng |
| 5,843,072 A | 12/1998 | Furumoto et al. |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,868,732 A | 2/1999 | Waldman et al. |
| 5,871,479 A | 2/1999 | Furumoto et al. |
| 5,871,480 A | 2/1999 | Tankovich |
| 5,879,159 A | 3/1999 | Cipolla |
| 5,879,346 A | 3/1999 | Waldman et al. |
| 5,879,376 A | 3/1999 | Miller |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,893,885 A | 4/1999 | Webster, Jr. |
| 5,895,350 A | 4/1999 | Hori |
| 5,897,549 A | 4/1999 | Tankovich |
| 5,906,609 A | 5/1999 | Assa et al. |
| 5,908,418 A | 6/1999 | Dority et al. |
| 5,908,731 A | 6/1999 | Leenders et al. |
| 5,913,883 A | 6/1999 | Alexander et al. |
| 5,916,211 A | 6/1999 | Quon et al. |
| 5,919,601 A | 7/1999 | Nguyen et al. |
| 5,920,374 A | 7/1999 | Vaphiades et al. |
| 5,921,926 A | 7/1999 | Rolland et al. |
| 5,928,222 A | 7/1999 | Kleinerman |
| 5,935,124 A | 8/1999 | Klumb et al. |
| 5,944,687 A | 8/1999 | Benett et al. |
| 5,944,748 A | 8/1999 | Mager et al. |
| 5,948,011 A | 9/1999 | Knowlton |
| 5,948,596 A | 9/1999 | Zhong et al. |
| 5,949,222 A | 9/1999 | Buono |
| 5,951,543 A | 9/1999 | Brauer |
| 5,954,710 A | 9/1999 | Paolini et al. |
| 5,955,490 A | 9/1999 | Kennedy et al. |
| 5,957,915 A | 9/1999 | Trost |
| 5,964,749 A | 10/1999 | Eckhouse et al. |
| 5,968,033 A | 10/1999 | Fuller et al. |
| 5,968,034 A | 10/1999 | Fullmer et al. |
| 5,971,976 A | 10/1999 | Wang et al. |
| 5,974,059 A | 10/1999 | Dawson |
| 5,974,616 A | 11/1999 | Dreyfus |
| 5,976,123 A | 11/1999 | Baumgardner et al. |
| 5,977,723 A | 11/1999 | Yoon |
| 5,979,454 A | 11/1999 | Anvari et al. |
| 5,983,900 A | 11/1999 | Clement et al. |
| 5,984,915 A | 11/1999 | Loeb et al. |
| 6,004,723 A | 12/1999 | Figov |
| 6,007,219 A | 12/1999 | O'Meara |
| 6,015,404 A | 1/2000 | Altshuler et al. |
| 6,017,677 A | 1/2000 | Maemoto et al. |
| 6,022,316 A | 2/2000 | Eppstein et al. |
| 6,022,346 A | 2/2000 | Panescu et al. |
| 6,024,095 A | 2/2000 | Stanley, III |
| 6,026,828 A | 2/2000 | Altshuler |
| 6,027,493 A | 2/2000 | Donitzky et al. |
| 6,027,495 A | 2/2000 | Miller |
| 6,028,694 A | 2/2000 | Schmidt |
| 6,029,303 A | 2/2000 | Dewan |
| 6,029,304 A | 2/2000 | Hulke et al. |
| 6,030,378 A | 2/2000 | Stewart |
| 6,030,399 A | 2/2000 | Ignotz et al. |
| 6,032,071 A | 2/2000 | Binder |
| RE36,634 E | 3/2000 | Ghaffari |
| 6,033,431 A | 3/2000 | Segal |
| 6,036,684 A | 3/2000 | Tankovich et al. |
| 6,044,514 A | 4/2000 | Kaneda et al. |
| 6,045,548 A | 4/2000 | Furumoto et al. |
| 6,050,990 A | 4/2000 | Tankovich et al. |
| D424,197 S | 5/2000 | Sydlowski et al. |
| 6,056,548 A | 5/2000 | Neuberger et al. |
| 6,056,738 A | 5/2000 | Marchitto et al. |
| 6,058,937 A | 5/2000 | Doiron et al. |
| 6,059,820 A | 5/2000 | Baronov |
| 6,063,108 A | 5/2000 | Salansky et al. |
| 6,068,963 A | 5/2000 | Aoshima |
| 6,070,092 A | 5/2000 | Kazama et al. |
| 6,071,239 A | 6/2000 | Cribbs et al. |
| 6,074,382 A | 6/2000 | Asah et al. |
| 6,077,294 A | 6/2000 | Cho et al. |
| 6,080,146 A | 6/2000 | Altshuler et al. |
| 6,080,147 A | 6/2000 | Tobinick |
| 6,083,217 A | 7/2000 | Tankovich |
| 6,086,363 A | 7/2000 | Moran et al. |
| 6,086,558 A | 7/2000 | Bower et al. |
| 6,086,580 A | 7/2000 | Mordon et al. |
| 6,090,524 A | 7/2000 | Deboer et al. |
| 6,132,929 A | 7/2000 | Nakamura |
| 6,094,767 A | 8/2000 | Iimura |
| 6,096,028 A | 8/2000 | Bahmanyar et al. |
| 6,096,029 A | 8/2000 | O'Donnell, Jr. |
| 6,096,209 A | 8/2000 | O'Brien et al. |
| 6,099,521 A | 8/2000 | Shadduck |
| 6,101,207 A | 8/2000 | Ilorinne |
| 6,104,959 A | 8/2000 | Spertell |
| 6,106,293 A | 8/2000 | Wiesel |
| 6,106,294 A | 8/2000 | Daniel |
| 6,110,195 A | 8/2000 | Xie et al. |
| 6,112,123 A | 8/2000 | Kelleher et al. |
| 6,113,559 A | 9/2000 | Klopotek |
| 6,117,129 A | 9/2000 | Mukai |
| 6,120,497 A | 9/2000 | Anderson et al. |
| 6,126,655 A | 10/2000 | Domankevitz et al. |
| 6,129,723 A | 10/2000 | Anderson |
| 6,135,774 A | 10/2000 | Hack et al. |
| 6,142,650 A | 11/2000 | Brown et al. |
| 6,142,939 A | 11/2000 | Eppstein et al. |
| 6,149,644 A | 11/2000 | Xie |
| 6,149,895 A | 11/2000 | Kutsch |
| 6,153,352 A | 11/2000 | Oohashi et al. |
| 6,159,203 A | 12/2000 | Sinofsky et al. |
| 6,159,236 A | 12/2000 | Biel |
| 6,162,055 A | 12/2000 | Montgomery et al. |
| 6,162,211 A | 12/2000 | Tankovich et al. |
| 6,162,212 A | 12/2000 | Kreindel et al. |
| 6,162,215 A | 12/2000 | Feng |
| 6,162,218 A | 12/2000 | Elbrecht et al. |
| 6,164,837 A | 12/2000 | Haake et al. |
| 6,171,300 B1 | 1/2001 | Adams |
| 6,171,301 B1 | 1/2001 | Nelson |
| 6,171,302 B1 | 1/2001 | Talpalriu et al. |
| 6,171,332 B1 | 1/2001 | Whitehurst |
| 6,173,202 B1 | 1/2001 | Eppstein |
| 6,174,325 B1 | 1/2001 | Eckhouse |
| 6,176,854 B1 | 1/2001 | Cone |
| 6,177,230 B1 | 1/2001 | Kawamura |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,190,825 B1 | 2/2001 | Denzinger et al. |
| 6,190,831 B1 | 2/2001 | Leon et al. |
| 6,197,020 B1 | 3/2001 | Donnell, Jr. |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,210,425 B1 | 4/2001 | Chen |
| 6,210,426 B1 | 4/2001 | Cho et al. |
| 6,214,034 B1 | 4/2001 | Azar |
| 6,221,068 B1 | 4/2001 | Fried et al. |
| 6,221,095 B1 | 4/2001 | Van Zuylen et al. |
| 6,228,074 B1 | 5/2001 | Almeida |
| 6,228,075 B1 | 5/2001 | Furumoto |

(56) References Cited

U.S. PATENT DOCUMENTS

| | | |
|---|---|---|
| 6,229,831 B1 | 5/2001 | Nightingale et al. |
| 6,235,015 B1 | 5/2001 | Mead et al. |
| 6,235,016 B1 | 5/2001 | Stewart |
| 6,236,891 B1 | 5/2001 | Ingle et al. |
| 6,238,839 B1 | 5/2001 | Tomita et al. |
| 6,239,442 B1 | 5/2001 | Iimura |
| 6,240,306 B1 | 5/2001 | Rohrscheib et al. |
| 6,240,925 B1 | 6/2001 | McMillan et al. |
| 6,245,093 B1 | 6/2001 | Li et al. |
| 6,245,486 B1 | 6/2001 | Teng |
| 6,246,710 B1 | 6/2001 | Furumoto |
| 6,248,103 B1 | 6/2001 | Tannenbaum et al. |
| 6,248,503 B1 | 6/2001 | Vermeersch et al. |
| 6,251,127 B1 | 6/2001 | Biel |
| 6,246,740 B1 | 7/2001 | Nguyen et al. |
| 6,254,388 B1 | 7/2001 | Yarborough |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,883 B1 | 8/2001 | Furumoto |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,282,442 B1 | 8/2001 | Destefano et al. |
| 6,283,956 B1 | 9/2001 | McDaniel |
| 6,287,549 B1 | 9/2001 | Sumian et al. |
| 6,290,496 B1 | 9/2001 | Azar et al. |
| 6,290,712 B1 | 9/2001 | Nordquist et al. |
| 6,290,713 B1 | 9/2001 | Russell |
| 6,294,311 B1 | 9/2001 | Shimazu et al. |
| 6,306,130 B1 | 10/2001 | Anderson et al. |
| 6,306,160 B1 | 10/2001 | Nidetzky |
| 6,233,584 B1 | 11/2001 | Ingle et al. |
| 6,315,772 B1 | 11/2001 | Marchitto et al. |
| 6,317,624 B1 | 11/2001 | Kollias et al. |
| 6,319,274 B1 | 11/2001 | Shadduck |
| 6,322,584 B2 | 11/2001 | Ingle et al. |
| 6,325,769 B1 | 12/2001 | Klopotek |
| 6,327,506 B1 | 12/2001 | Yogo et al. |
| 6,328,733 B1 | 12/2001 | Trost |
| 6,331,111 B1 | 12/2001 | Cao |
| 6,332,891 B1 | 12/2001 | Himes |
| 6,338,855 B1 | 1/2002 | Albacarys et al. |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,346,365 B1 | 2/2002 | Kawauchi et al. |
| 6,350,261 B1 | 2/2002 | Domankevitz et al. |
| 6,350,276 B1 | 2/2002 | Knowlton |
| 6,352,811 B1 | 3/2002 | Patel et al. |
| 6,354,370 B1 | 3/2002 | Miller et al. |
| 6,355,054 B1 | 3/2002 | Neuberger |
| 6,358,242 B1 | 3/2002 | Cecchetti |
| 6,358,272 B1 | 3/2002 | Wilden |
| 6,358,669 B1 | 3/2002 | Savarair-Hauck et al. |
| 6,364,872 B1 | 4/2002 | Hsia et al. |
| 6,383,176 B1 | 5/2002 | Connors et al. |
| 6,383,177 B1 | 5/2002 | Balle-Petersen |
| 6,387,089 B1 | 5/2002 | Kreindel et al. |
| 6,387,353 B1 | 5/2002 | Jensen et al. |
| 6,391,022 B1 | 5/2002 | Furumoto et al. |
| 6,394,949 B1 | 5/2002 | Crowley et al. |
| 6,395,016 B1 | 5/2002 | Oron et al. |
| 6,398,801 B1 | 6/2002 | Clement et al. |
| 6,400,011 B1 | 6/2002 | Miki |
| 6,402,739 B1 | 6/2002 | Neev |
| 6,405,732 B1 | 6/2002 | Edwards et al. |
| 6,406,474 B1 | 6/2002 | Neuberger et al. |
| 6,409,665 B1 | 6/2002 | Scott et al. |
| 6,409,723 B1 | 6/2002 | Edwards |
| 6,413,267 B1 | 7/2002 | Dumoulin-White |
| 6,416,319 B1 | 7/2002 | Cipolla |
| 6,419,389 B1 | 7/2002 | Fuchs et al. |
| 6,423,462 B1 | 7/2002 | Kunita |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,440,633 B1 | 8/2002 | Kawauchi |
| 6,443,946 B2 | 9/2002 | Clement et al. |
| 6,443,978 B1 | 9/2002 | Zharov |
| 6,447,503 B1 | 9/2002 | Wynne et al. |
| 6,447,504 B1 | 9/2002 | Ben-Haim et al. |
| 6,451,007 B1 | 9/2002 | Koop et al. |
| 6,454,790 B1 | 9/2002 | Neuberger et al. |
| 6,459,919 B1 | 10/2002 | Lys et al. |
| 6,461,296 B1 | 10/2002 | Desai |
| 6,464,694 B1 | 10/2002 | Massengill |
| 6,468,717 B2 | 10/2002 | Kita et al. |
| 6,470,216 B1 | 10/2002 | Mulholland |
| 6,471,712 B2 | 10/2002 | Burres |
| 6,471,716 B1 | 10/2002 | Pecukonis |
| 6,475,211 B2 | 11/2002 | Chess et al. |
| 6,482,199 B1 | 11/2002 | Neev |
| 6,484,052 B1 | 11/2002 | Visuri et al. |
| 6,485,413 B1 | 11/2002 | Boppart et al. |
| 6,491,685 B2 | 12/2002 | Visuri et al. |
| 6,493,608 B1 | 12/2002 | Niemeyer |
| 6,494,900 B1 | 12/2002 | Salansky et al. |
| 6,497,702 B1 | 12/2002 | Bernaz |
| 6,503,269 B2 | 1/2003 | Nield et al. |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,519,376 B2 | 2/2003 | Biagi et al. |
| 6,525,819 B1 | 2/2003 | Delawter et al. |
| 6,527,716 B1 | 3/2003 | Eppstein |
| 6,527,764 B1 | 3/2003 | Neuberger et al. |
| 6,529,540 B1 | 3/2003 | Demmer et al. |
| 6,530,915 B1 | 3/2003 | Eppstein et al. |
| 6,530,916 B1 | 3/2003 | Shimmick |
| 6,537,270 B1 | 3/2003 | Elbrecht et al. |
| 6,544,257 B2 | 4/2003 | Nagage et al. |
| 6,547,780 B1 | 4/2003 | Sinofsky |
| 6,551,346 B2 | 4/2003 | Crossley |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger |
| 6,569,155 B1 | 5/2003 | Connors et al. |
| 6,570,892 B1 | 5/2003 | Lin et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,595,934 B1 | 7/2003 | Hissong et al. |
| 6,600,951 B1 | 7/2003 | Anderson |
| 6,602,245 B1 | 8/2003 | Thiberg |
| 6,602,275 B1 | 8/2003 | Sullivan |
| 6,603,988 B2 | 8/2003 | Dowlatshahi |
| 6,605,080 B1 | 8/2003 | Altshuler et al. |
| 6,605,083 B2 | 8/2003 | Clement et al. |
| 6,606,755 B1 | 8/2003 | Robinson et al. |
| 6,607,525 B2 | 8/2003 | France et al. |
| 6,610,052 B2 | 8/2003 | Furumoto |
| 6,613,040 B2 | 9/2003 | Tankovich et al. |
| 6,616,447 B1 | 9/2003 | Rizoiu et al. |
| 6,616,451 B1 | 9/2003 | Rizoiu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,652,459 B2 | 11/2003 | Payne et al. |

(56) References Cited

U.S. PATENT DOCUMENTS

| | | |
|---|---|---|
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,666,856 B2 | 12/2003 | Connors et al. |
| 6,669,685 B1 | 12/2003 | Rizoiu et al. |
| 6,675,425 B1 | 1/2004 | Iimura |
| 6,676,654 B1 | 1/2004 | Balle-Petersen |
| 6,679,837 B2 | 1/2004 | Daikuzono |
| 6,682,523 B2 | 1/2004 | Shadduck |
| 6,682,524 B1 | 1/2004 | Elbrecht et al. |
| 6,685,639 B1 | 2/2004 | Wang et al. |
| 6,685,699 B1 | 2/2004 | Eppstein et al. |
| 6,685,722 B1 | 2/2004 | Rosenbluth et al. |
| 6,689,124 B1 | 2/2004 | Thiberg |
| 6,692,456 B1 | 2/2004 | Eppstein et al. |
| 6,692,517 B2 | 2/2004 | Cho et al. |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,724,958 B1 | 4/2004 | German et al. |
| 6,726,681 B2 | 4/2004 | Grasso et al. |
| 6,736,807 B2 | 5/2004 | Yamazaki et al. |
| 6,743,222 B2 | 6/2004 | Durkin et al. |
| 6,746,444 B2 | 6/2004 | Key |
| 6,749,623 B1 | 6/2004 | His et al. |
| 6,755,647 B2 | 6/2004 | Melikechi et al. |
| 6,770,069 B1 | 8/2004 | Hobart et al. |
| 6,772,053 B2 | 8/2004 | Niemeyer |
| 6,790,205 B1 | 9/2004 | Yamazaki et al. |
| 6,800,122 B2 | 10/2004 | Anderson et al. |
| 6,801,595 B2 | 10/2004 | Grodzins et al. |
| 6,808,331 B2 | 10/2004 | Hall et al. |
| 6,808,532 B2 | 10/2004 | Andersen et al. |
| 6,824,542 B2 | 11/2004 | Jay |
| RE38,670 E | 12/2004 | Asah et al. |
| 6,858,009 B2 | 2/2005 | Kawata et al. |
| 6,860,879 B2 | 3/2005 | Irion et al. |
| 6,860,896 B2 | 3/2005 | Leber et al. |
| 6,862,771 B1 | 3/2005 | Muller |
| 6,863,781 B2 | 3/2005 | Nocera et al. |
| 6,872,203 B2 | 3/2005 | Shafirstein et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,905,492 B2 | 6/2005 | Zvuloni et al. |
| 6,916,316 B2 | 7/2005 | Jay |
| 6,917,715 B2 | 7/2005 | Berstis |
| 6,936,046 B2 | 8/2005 | Hissong et al. |
| 6,942,658 B1 | 9/2005 | Rizoiu et al. |
| 6,953,341 B2 | 10/2005 | Black |
| 6,974,450 B2 | 12/2005 | Weber et al. |
| 6,974,451 B2 | 12/2005 | Altshuler et al. |
| 6,976,985 B2 | 12/2005 | Altshuler et al. |
| 6,986,903 B2 | 1/2006 | Zulli et al. |
| 6,989,007 B2 | 1/2006 | Shadduck |
| 6,989,023 B2 | 1/2006 | Black |
| 6,991,644 B2 | 1/2006 | Spooner et al. |
| 6,997,923 B2 | 2/2006 | Anderson et al. |
| 7,001,413 B2 | 2/2006 | Butler |
| 7,006,223 B2 | 2/2006 | Mullani |
| 7,006,874 B2 | 2/2006 | Knowlton |
| 7,018,396 B2 | 3/2006 | Sierra et al. |
| 7,029,469 B2 | 4/2006 | Vasily |
| 7,033,349 B2 | 4/2006 | Key |
| 7,041,094 B2 | 5/2006 | Connors et al. |
| 7,041,100 B2 | 5/2006 | Kreindel |
| 7,044,959 B2 | 5/2006 | Anderson et al. |
| 7,060,061 B2 | 6/2006 | Altshuler et al. |
| 7,066,733 B2 | 6/2006 | Logan et al. |
| 7,070,611 B2 | 7/2006 | Biel |
| 7,077,840 B2 | 7/2006 | Altshuler et al. |
| 7,081,128 B2 | 7/2006 | Hart et al. |
| 7,097,639 B1 | 8/2006 | Almeida |
| 7,097,656 B1 | 8/2006 | Akopov et al. |
| 7,104,985 B2 | 9/2006 | Martinelli |
| 7,118,562 B2 | 10/2006 | Furumoto |
| 7,118,563 B2 | 10/2006 | Weckwerth et al. |
| 7,135,033 B2 | 11/2006 | Altshuler et al. |
| 7,144,247 B2 | 12/2006 | Black |
| 7,144,248 B2 | 12/2006 | Irwin |
| 7,145,105 B2 | 12/2006 | Gaulard |
| 7,145,108 B2 | 12/2006 | Kanel et al. |
| 7,160,289 B2 | 1/2007 | Cohen |
| 7,170,034 B2 | 1/2007 | Shalev |
| 7,175,617 B2 | 2/2007 | Jay |
| 7,182,760 B2 | 2/2007 | Kubota |
| 7,198,634 B2 | 4/2007 | Harth et al. |
| 7,202,446 B2 | 4/2007 | Shalev |
| 7,204,832 B2 | 4/2007 | Altshuler et al. |
| 7,216,055 B1 | 5/2007 | Horton et al. |
| 7,217,265 B2 | 5/2007 | Hennings et al. |
| 7,217,267 B2 | 5/2007 | Jay |
| 7,220,254 B2 | 5/2007 | Altshuler et al. |
| 7,223,270 B2 | 5/2007 | Altshuler et al. |
| 7,223,281 B2 | 5/2007 | Altshuler et al. |
| 7,255,691 B2 | 8/2007 | Tolkoff et al. |
| 7,274,155 B2 | 9/2007 | Inochkin et al. |
| 7,276,058 B2 | 10/2007 | Altshuler et al. |
| 7,280,866 B1 | 10/2007 | McIntosh et al. |
| 7,282,060 B2 | 10/2007 | DeBenedictis |
| 7,282,723 B2 | 10/2007 | Schomaket et al. |
| 7,291,140 B2 | 11/2007 | MacFarland et al. |
| 7,291,141 B2 | 11/2007 | Harvey |
| 7,309,335 B2 | 12/2007 | Altshuler et al. |
| 7,311,722 B2 | 12/2007 | Larsen |
| 7,322,972 B2 | 1/2008 | Viator et al. |
| 7,329,273 B2 | 2/2008 | Altshuler et al. |
| 7,329,274 B2 | 2/2008 | Altshuler et al. |
| 7,331,953 B2 | 2/2008 | Manstein et al. |
| 7,331,964 B2 | 2/2008 | Maricle et al. |
| 7,333,698 B2 | 2/2008 | Israel |
| 7,333,841 B2 | 2/2008 | Maruo et al. |
| 7,351,252 B2 | 4/2008 | Altshuler et al. |
| 7,354,448 B2 | 4/2008 | Altshuler et al. |
| 7,422,598 B2 | 9/2008 | Altshuler et al. |
| 7,423,767 B2 | 9/2008 | Steinsiek et al. |
| 7,431,719 B2 | 10/2008 | Altshuler |
| 7,436,863 B2 | 10/2008 | Matsuda et al. |
| 7,500,956 B1 | 3/2009 | Wilk |
| 7,531,967 B2 | 5/2009 | Inochkin et al. |
| 7,540,869 B2 | 6/2009 | Altshuler et al. |
| 7,553,308 B2 | 6/2009 | Jay |
| 7,586,957 B2 | 9/2009 | Sierra et al. |
| 7,588,547 B2 | 9/2009 | Deem et al. |
| 7,624,640 B2 | 12/2009 | Maris et al. |
| 7,647,092 B2 | 1/2010 | Motz et al. |
| 7,699,058 B1 | 4/2010 | Jay |
| 7,722,600 B2 | 5/2010 | Connors et al. |
| 7,758,621 B2 | 7/2010 | Altshuler et al. |
| 7,763,016 B2 | 7/2010 | Altshuler et al. |
| 7,839,972 B2 | 11/2010 | Ruchala et al. |
| 7,856,985 B2 * | 12/2010 | Mirkov ............... A61N 5/0616 128/898 |
| 7,860,554 B2 | 12/2010 | Leonardi |
| 7,929,579 B2 | 4/2011 | Hohm et al. |
| 7,931,028 B2 | 4/2011 | Jay |
| 7,935,107 B2 | 5/2011 | Altshuler et al. |
| 7,938,821 B2 | 5/2011 | Chan et al. |
| 7,942,869 B2 | 5/2011 | Houbolt et al. |
| 7,942,915 B2 | 5/2011 | Altshuler et al. |
| 7,942,916 B2 | 5/2011 | Altshuler et al. |
| 7,998,181 B2 | 8/2011 | Nightingale et al. |
| 8,002,768 B1 | 8/2011 | Altshuler et al. |
| 8,027,710 B1 | 9/2011 | Dannan |
| 8,109,924 B2 | 2/2012 | Altshuler |

(56) References Cited

U.S. PATENT DOCUMENTS

| | | |
|---|---|---|
| 8,113,209 B2 | 2/2012 | Masotti et al. |
| 8,182,473 B2 | 5/2012 | Altshuler et al. |
| 8,317,779 B2 | 11/2012 | Mirkov et al. |
| 8,322,348 B2 | 12/2012 | Mirkov et al. |
| 8,328,794 B2 | 12/2012 | Altshuler et al. |
| 8,328,796 B2 | 12/2012 | Altshuler et al. |
| 8,346,347 B2 | 1/2013 | Altshuler et al. |
| 8,357,145 B2 | 1/2013 | Hennings et al. |
| 8,378,322 B2 | 2/2013 | Dahm et al. |
| 8,439,940 B2 | 5/2013 | Chomas et al. |
| 11,095,087 B2 * | 8/2021 | Sierra ............... H01S 3/1611 |
| 2001/0007068 A1 | 7/2001 | Ota |
| 2001/0008973 A1 | 7/2001 | Van Zuylen et al. |
| 2001/0016732 A1 | 8/2001 | Hobart et al. |
| 2001/0023363 A1 | 9/2001 | Harth et al. |
| 2001/0024777 A1 | 9/2001 | Azar et al. |
| 2001/0025173 A1 | 9/2001 | Ritchie et al. |
| 2001/0029956 A1 | 10/2001 | Argenta et al. |
| 2001/0041886 A1 | 11/2001 | Durkin et al. |
| 2001/0046652 A1 | 11/2001 | Ostler et al. |
| 2001/0048077 A1 | 12/2001 | Afanassieva |
| 2002/0002367 A1 | 1/2002 | Tankovich et al. |
| 2002/0004066 A1 | 1/2002 | Stanley et al. |
| 2002/0005475 A1 | 1/2002 | Zenzie |
| 2002/0013572 A1 | 1/2002 | Berlin |
| 2002/0015911 A1 | 2/2002 | Nakamura |
| 2002/0016587 A1 | 2/2002 | Furumoto |
| 2002/0018754 A1 | 2/2002 | Sagel et al. |
| 2002/0019624 A1 | 2/2002 | Clement et al. |
| 2002/0019625 A1 | 2/2002 | Azar |
| 2002/0026225 A1 | 2/2002 | Segal |
| 2002/0028404 A1 | 3/2002 | Nakamura |
| 2002/0029071 A1 | 3/2002 | Whitehurst |
| 2002/0032437 A1 | 3/2002 | Andrews et al. |
| 2002/0039702 A1 | 4/2002 | Hotta |
| 2002/0045891 A1 | 4/2002 | Clement et al. |
| 2002/0048722 A1 | 4/2002 | Aoshima |
| 2002/0049432 A1 | 4/2002 | Mukai |
| 2002/0049483 A1 | 4/2002 | Knowlton |
| 2002/0058890 A1 | 5/2002 | Visuri et al. |
| 2002/0071287 A1 | 6/2002 | Haase |
| 2002/0071827 A1 | 6/2002 | Petersen et al. |
| 2002/0072676 A1 | 6/2002 | Afanassieva |
| 2002/0081555 A1 | 6/2002 | Wiesel |
| 2002/0090725 A1 | 7/2002 | Simpson et al. |
| 2002/0091377 A1 | 7/2002 | Anderson et al. |
| 2002/0108193 A1 | 8/2002 | Gruber |
| 2002/0111546 A1 | 8/2002 | Cook et al. |
| 2002/0111610 A1 | 8/2002 | Nordquist |
| 2002/0120256 A1 | 8/2002 | Furuno et al. |
| 2002/0123745 A1 | 9/2002 | Svaasand et al. |
| 2002/0125230 A1 | 9/2002 | Haight et al. |
| 2002/0127224 A1 | 9/2002 | Chen |
| 2002/0128635 A1 | 9/2002 | Altshuler et al. |
| 2002/0128695 A1 | 9/2002 | Harth et al. |
| 2002/0128696 A1 | 9/2002 | Pearl |
| 2002/0151878 A1 | 10/2002 | Shimmick et al. |
| 2002/0151879 A1 | 10/2002 | Loeb |
| 2002/0160299 A1 | 10/2002 | Asawa et al. |
| 2002/0161357 A1 | 10/2002 | Anderson et al. |
| 2002/0161418 A1 | 10/2002 | Wilkens et al. |
| 2002/0167974 A1 | 11/2002 | Kennedy et al. |
| 2002/0173723 A1 | 11/2002 | Lewis |
| 2002/0173777 A1 | 11/2002 | Sand |
| 2002/0173780 A1 | 11/2002 | Altshuler et al. |
| 2002/0173781 A1 | 11/2002 | Cense et al. |
| 2002/0173782 A1 | 11/2002 | Cense et al. |
| 2002/0182563 A1 | 12/2002 | Boutoussov et al. |
| 2002/0183808 A1 | 12/2002 | Biel |
| 2002/0198517 A1 | 12/2002 | Alfano et al. |
| 2003/0004499 A1 | 1/2003 | McDaniel |
| 2003/0009158 A1 | 1/2003 | Perricone |
| 2003/0009205 A1 | 1/2003 | Biel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028186 A1 | 2/2003 | Kreintel |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055413 A1 | 3/2003 | Altshuler et al. |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |
| 2003/0073989 A1 | 4/2003 | Hoey et al. |
| 2003/0083649 A1 | 5/2003 | Margaron et al. |
| 2003/0084534 A1 | 5/2003 | Kaizuka |
| 2003/0092982 A1 | 5/2003 | Eppstein |
| 2003/0097122 A1 | 5/2003 | Ganz et al. |
| 2003/0100936 A1 | 5/2003 | Altshuler et al. |
| 2003/0104340 A1 | 6/2003 | Clemans |
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | Haber |
| 2003/0152528 A1 | 8/2003 | Singh et al. |
| 2003/0158550 A1 | 8/2003 | Ganz et al. |
| 2003/0163884 A1 | 9/2003 | Weihrauch |
| 2003/0167080 A1 | 9/2003 | Hart et al. |
| 2003/0169433 A1 | 9/2003 | Koele et al. |
| 2003/0181896 A1 | 9/2003 | Zvuloni et al. |
| 2003/0187319 A1 | 10/2003 | Kaneko |
| 2003/0187383 A1 | 10/2003 | Weber et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216719 A1 | 11/2003 | DeBenedictis |
| 2003/0216795 A1 | 11/2003 | Harth et al. |
| 2003/0232303 A1 | 12/2003 | Black |
| 2003/0233138 A1 | 12/2003 | Spooner |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019120 A1 | 1/2004 | Vargas et al. |
| 2004/0019990 A1 | 2/2004 | Farrell et al. |
| 2004/0024388 A1 | 2/2004 | Altshuler |
| 2004/0024430 A1 | 2/2004 | Bader et al. |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0036975 A1 | 2/2004 | Slatkine |
| 2004/0054248 A1 | 3/2004 | Kimchy et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0092506 A1 | 5/2004 | Thompson et al. |
| 2004/0093042 A1 | 5/2004 | Altshuler et al. |
| 2004/0093043 A1 | 5/2004 | Edel et al. |
| 2004/0098070 A1 | 5/2004 | Mohr et al. |
| 2004/0105611 A1 | 6/2004 | Bischel et al. |
| 2004/0111031 A1 | 6/2004 | Alfano et al. |
| 2004/0111086 A1 | 6/2004 | Trombly |
| 2004/0111132 A1 | 6/2004 | Shenderova et al. |
| 2004/0116984 A1 | 6/2004 | Spooner et al. |
| 2004/0122311 A1 | 6/2004 | Cosman |
| 2004/0133251 A1 | 7/2004 | Altshuler et al. |
| 2004/0143181 A1 | 7/2004 | Damasio et al. |
| 2004/0143247 A1 | 7/2004 | Anderson et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162490 A1 | 8/2004 | Soltz et al. |
| 2004/0162549 A1 | 8/2004 | Altshuler |
| 2004/0162596 A1 | 8/2004 | Altshuler et al. |
| 2004/0167502 A1 | 8/2004 | Weckwerth et al. |
| 2004/0176754 A1 | 9/2004 | Island et al. |
| 2004/0176764 A1 | 9/2004 | Dant |

(56) References Cited

U.S. PATENT DOCUMENTS

| | | |
|---|---|---|
| 2004/0186465 A1 | 9/2004 | Francischelli |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199079 A1 | 10/2004 | Chuck et al. |
| 2004/0199151 A1 | 10/2004 | Neuberger |
| 2004/0199227 A1 | 10/2004 | Altshuler et al. |
| 2004/0204745 A1 | 10/2004 | Altshuler et al. |
| 2004/0208918 A1 | 10/2004 | Koch et al. |
| 2004/0210275 A1 | 10/2004 | Town et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2004/0249261 A1 | 12/2004 | Torchia et al. |
| 2004/0260210 A1 | 12/2004 | Ella et al. |
| 2005/0015077 A1 | 1/2005 | Kuklin et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis |
| 2005/0049658 A1 | 3/2005 | Connors et al. |
| 2005/0063931 A1 | 3/2005 | Paus et al. |
| 2005/0065502 A1 | 3/2005 | Stoltz |
| 2005/0065531 A1 | 3/2005 | Cohen |
| 2005/0074038 A1 | 4/2005 | Khaydarov |
| 2005/0080404 A1 | 4/2005 | Jones et al. |
| 2005/0085875 A1 | 4/2005 | Van Zuylen |
| 2005/0102213 A1 | 5/2005 | Savasoglu et al. |
| 2005/0107849 A1 | 5/2005 | Altshuler et al. |
| 2005/0113815 A1 | 5/2005 | Ritchie et al. |
| 2005/0113890 A1 | 5/2005 | Ritchie et al. |
| 2005/0116673 A1 | 6/2005 | Carl et al. |
| 2005/0131400 A1 | 6/2005 | Hennings et al. |
| 2005/0143719 A1 | 6/2005 | Sink |
| 2005/0143723 A1 | 6/2005 | Zvuloni et al. |
| 2005/0154380 A1 | 7/2005 | DeBenedictis |
| 2005/0165315 A1 | 7/2005 | Zuluga et al. |
| 2005/0165393 A1 | 7/2005 | Eppstein |
| 2005/0168158 A1 | 8/2005 | Inochkin et al. |
| 2005/0170313 A1 | 8/2005 | Pitz et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0177139 A1 | 8/2005 | Yamazaki et al. |
| 2005/0177142 A1 | 8/2005 | Jay |
| 2005/0182389 A1 | 8/2005 | Laporte et al. |
| 2005/0197681 A1 | 9/2005 | Barolet et al. |
| 2005/0203496 A1 | 9/2005 | Ritchie et al. |
| 2005/0203497 A1 | 9/2005 | Speeg et al. |
| 2005/0215988 A1 | 9/2005 | Altshuler et al. |
| 2005/0220726 A1 | 10/2005 | Pauly et al. |
| 2005/0222556 A1 | 10/2005 | Arivra et al. |
| 2005/0245917 A1 | 11/2005 | Strassl et al. |
| 2005/0251116 A1 | 11/2005 | Steinke et al. |
| 2005/0251117 A1 | 11/2005 | Anderson et al. |
| 2005/0251118 A1 | 11/2005 | Anderson et al. |
| 2005/0251120 A1 | 11/2005 | Anderson et al. |
| 2005/0257612 A1 | 11/2005 | Hiemer et al. |
| 2005/0281530 A1 | 12/2005 | Rizoiu et al. |
| 2006/0004306 A1 | 1/2006 | Altshuler et al. |
| 2006/0004347 A1 | 1/2006 | Altshuler et al. |
| 2006/0007965 A1 | 1/2006 | Tankovich et al. |
| 2006/0009750 A1 | 1/2006 | Altshuler et al. |
| 2006/0013533 A1 | 1/2006 | Slatkine et al. |
| 2006/0020309 A1 | 1/2006 | Altshuler et al. |
| 2006/0047281 A1 | 3/2006 | Kreindel et al. |
| 2006/0052661 A1 | 3/2006 | Gannot et al. |
| 2006/0056589 A1 | 3/2006 | Engelward |
| 2006/0058712 A1 | 3/2006 | Altshuler et al. |
| 2006/0062448 A1 | 3/2006 | Hirsch et al. |
| 2006/0079947 A1 | 4/2006 | Tankovich et al. |
| 2006/0089687 A1 | 4/2006 | Spooner et al. |
| 2006/0094988 A1 | 5/2006 | Tosaya et al. |
| 2006/0100677 A1 | 5/2006 | Blumenkranz et al. |
| 2006/0116671 A1 | 6/2006 | Slayton et al. |
| 2006/0118127 A1 | 6/2006 | Chinn |
| 2006/0122584 A1 | 6/2006 | Bommannan et al. |
| 2006/0122668 A1 | 6/2006 | Anderson et al. |
| 2006/0128771 A1 | 6/2006 | Mirkov et al. |
| 2006/0149343 A1 | 7/2006 | Altshulter et al. |
| 2006/0155266 A1 | 7/2006 | Manstein et al. |
| 2006/0161143 A1 | 7/2006 | Altshuler et al. |
| 2006/0173480 A1 | 8/2006 | Zhang |
| 2006/0194164 A1 | 8/2006 | Altshuler et al. |
| 2006/0206103 A1 | 9/2006 | Altshuler et al. |
| 2006/0217689 A1 | 9/2006 | Dick et al. |
| 2006/0224148 A1 | 10/2006 | Cho et al. |
| 2006/0247609 A1 | 11/2006 | Mirkov et al. |
| 2006/0253176 A1 | 11/2006 | Caruso et al. |
| 2006/0259102 A1 | 11/2006 | Slatkine |
| 2006/0265032 A1 | 11/2006 | Hennings |
| 2006/0271028 A1 | 11/2006 | Altshuler et al. |
| 2006/0282067 A1 | 12/2006 | Koop et al. |
| 2006/0287646 A1 | 12/2006 | Altshuler et al. |
| 2006/0293727 A1 | 12/2006 | Spooner et al. |
| 2006/0293728 A1 | 12/2006 | Roersma et al. |
| 2007/0027440 A1 | 2/2007 | Altshuler et al. |
| 2007/0038271 A1 | 2/2007 | Cole et al. |
| 2007/0038206 A1 | 3/2007 | Altshuler et al. |
| 2007/0049910 A1 | 3/2007 | Altshuler et al. |
| 2007/0060819 A1 | 3/2007 | Altshuler et al. |
| 2007/0060989 A1 | 3/2007 | Deem et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0088206 A1 | 4/2007 | Peyman |
| 2007/0093797 A1 | 4/2007 | Chan et al. |
| 2007/0105212 A1 | 5/2007 | Oldham et al. |
| 2007/0121069 A1 | 5/2007 | Andersen et al. |
| 2007/0123851 A1 | 5/2007 | Alejandro et al. |
| 2007/0213851 A1 | 5/2007 | Alejandro et al. |
| 2007/0142881 A1 | 6/2007 | Hennings |
| 2007/0159592 A1 | 7/2007 | Rylander et al. |
| 2007/0173749 A1 | 7/2007 | Williams et al. |
| 2007/0179378 A1 | 8/2007 | Boese et al. |
| 2007/0179470 A1 | 8/2007 | Toombs |
| 2007/0185552 A1 | 8/2007 | Masotti et al. |
| 2007/0191827 A1 | 8/2007 | Lischinsky et al. |
| 2007/0194717 A1 | 8/2007 | Belikov et al. |
| 2007/0198004 A1 | 8/2007 | Altshuler et al. |
| 2007/0208252 A1 | 9/2007 | Makower |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0219602 A1 | 9/2007 | Ostrovsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0244527 A1 | 10/2007 | Hatayama et al. |
| 2007/0255355 A1 | 11/2007 | Altshuler et al. |
| 2007/0260230 A1 | 11/2007 | Youngquist et al. |
| 2007/0264625 A1 | 11/2007 | DeBenedictis |
| 2007/0288071 A1 | 12/2007 | Rogers et al. |
| 2008/0003536 A1 | 1/2008 | Altshuler et al. |
| 2008/0004608 A1 | 1/2008 | Dacquay et al. |
| 2008/0004611 A1 | 1/2008 | Houbolt et al. |
| 2008/0009842 A1 | 1/2008 | Manstein et al. |
| 2008/0033516 A1 | 2/2008 | Altshuler et al. |
| 2008/0058782 A1 | 3/2008 | Frangcischelli |
| 2008/0058783 A1 | 3/2008 | Altshuler et al. |
| 2008/0082089 A1* | 4/2008 | Jones ............... A61N 5/0616 606/9 |
| 2008/0103565 A1 | 5/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0147054 A1 | 6/2008 | Altshuler et al. |
| 2008/0154157 A1 | 6/2008 | Altshuler et al. |
| 2008/0154247 A1 | 6/2008 | Dallarosa |
| 2008/0172047 A1 | 7/2008 | Altshuler et al. |

(56) References Cited

U.S. PATENT DOCUMENTS

| | | |
|---|---|---|
| 2008/0183162 A1 | 7/2008 | Altshuler et al. |
| 2008/0183250 A1 | 7/2008 | Tanojo et al. |
| 2008/0186591 A1 | 8/2008 | Altshuler et al. |
| 2008/0194969 A1 | 8/2008 | Werahera et al. |
| 2008/0195183 A1 | 8/2008 | Botchkareva et al. |
| 2008/0208105 A1 | 8/2008 | Zelickson et al. |
| 2008/0214988 A1 | 9/2008 | Altshuler et al. |
| 2008/0215038 A1 | 9/2008 | Bakker |
| 2008/0248554 A1 | 10/2008 | Merchant et al. |
| 2008/0262577 A1 | 10/2008 | Altshuler et al. |
| 2008/0294150 A1 | 11/2008 | Altshuler et al. |
| 2008/0294152 A1 | 11/2008 | Altshuler et al. |
| 2008/0294153 A1 | 11/2008 | Altshuler et al. |
| 2008/0306471 A1 | 12/2008 | Altshuler et al. |
| 2008/0319430 A1 | 12/2008 | Zenzie et al. |
| 2009/0018531 A1 | 1/2009 | Welches |
| 2009/0018624 A1 | 1/2009 | Levinson et al. |
| 2009/0024023 A1 | 1/2009 | Welches et al. |
| 2009/0024192 A1 | 1/2009 | Knowlton |
| 2009/0024193 A1 | 1/2009 | Altshuler et al. |
| 2009/0043294 A1 | 2/2009 | Island et al. |
| 2009/0048557 A1 | 2/2009 | Yeshurun et al. |
| 2009/0069741 A1 | 3/2009 | Altshuler et al. |
| 2009/0132011 A1 | 5/2009 | Altshuler et al. |
| 2009/0137995 A1 | 5/2009 | Altshuler et al. |
| 2009/0149843 A1 | 6/2009 | Smits et al. |
| 2009/0149844 A1 | 6/2009 | Altshuler et al. |
| 2009/0222068 A1 | 9/2009 | Oberreiter et al. |
| 2009/0227995 A1 | 9/2009 | Bhawalkar et al. |
| 2009/0248004 A1 | 10/2009 | Altshuler et al. |
| 2009/0254076 A1 | 10/2009 | Altshuler et al. |
| 2009/0287195 A1 | 11/2009 | Altshuler et al. |
| 2009/0292277 A1 | 11/2009 | Sierra et al. |
| 2009/0312749 A1 | 12/2009 | Pini et al. |
| 2010/0010507 A1 | 1/2010 | Kinoshita |
| 2010/0014543 A1* | 1/2010 | Ogilvy .................... H01S 3/109 372/19 |
| 2010/0015576 A1 | 1/2010 | Altshuler et al. |
| 2010/0021867 A1 | 1/2010 | Altshuler et al. |
| 2010/0036295 A1 | 2/2010 | Altshuler et al. |
| 2010/0049180 A1 | 2/2010 | Wells et al. |
| 2010/0109041 A1 | 5/2010 | Yin et al. |
| 2010/0123399 A1 | 5/2010 | Bollmann et al. |
| 2010/0145321 A1 | 6/2010 | Altshuler et al. |
| 2010/0195680 A1 | 8/2010 | Sierra et al. |
| 2010/0198134 A1 | 8/2010 | Eckhouse et al. |
| 2010/0204686 A1 | 8/2010 | Yaroslavsky et al. |
| 2010/0217248 A1 | 8/2010 | Mirkov et al. |
| 2010/0278756 A1 | 11/2010 | Chung et al. |
| 2010/0286673 A1 | 11/2010 | Altshuler et al. |
| 2010/0296531 A1* | 11/2010 | Hohm .................... A61B 18/203 372/12 |
| 2010/0298744 A1 | 11/2010 | Altshuler et al. |
| 2011/0046523 A1 | 2/2011 | Altshuler et al. |
| 2011/0087155 A1 | 4/2011 | Uhland et al. |
| 2011/0118722 A1 | 5/2011 | Lischinsky et al. |
| 2011/0137230 A1 | 6/2011 | Altshuler et al. |
| 2011/0152847 A1 | 6/2011 | Mirkov et al. |
| 2011/0172651 A1 | 7/2011 | Altshuler et al. |
| 2011/0184334 A1 | 7/2011 | Altshuler et al. |
| 2011/0207075 A1 | 8/2011 | Altshuler et al. |
| 2011/0257584 A1 | 10/2011 | Altshuler et al. |
| 2011/0267830 A1 | 11/2011 | Altshuler et al. |
| 2011/0306956 A1* | 12/2011 | Islam ...................... A61B 18/20 606/14 |
| 2011/0313408 A1 | 12/2011 | Tankovich et al. |
| 2012/0022510 A1 | 1/2012 | Welches et al. |
| 2012/0023129 A1 | 1/2012 | Vedula et al. |
| 2012/0083862 A1 | 4/2012 | Altshuler et al. |
| 2012/0099816 A1 | 4/2012 | Wilson |
| 2012/0116271 A1 | 5/2012 | Caruso et al. |
| 2012/0165725 A1 | 6/2012 | Chomas et al. |
| 2012/0277659 A1 | 11/2012 | Yaroslavsky et al. |
| 2012/0301842 A1 | 11/2012 | Altshuler et al. |
| 2014/0321484 A1* | 10/2014 | Sierra .................... H01S 3/1121 372/18 |
| 2015/0080863 A1* | 3/2015 | Welches ................ A61B 18/20 606/11 |
| 2015/0180193 A1 | 6/2015 | Sierra |
| 2016/0128777 A1* | 5/2016 | Welches ................ A61B 18/26 606/3 |
| 2016/0157935 A1* | 6/2016 | Jurna .................... A61B 18/203 606/9 |

FOREIGN PATENT DOCUMENTS

| | | |
|---|---|---|
| CN | 2053926 U | 3/1990 |
| CN | 1073607 A | 6/1993 |
| CN | 1182572 A | 5/1998 |
| CN | 1351483 A | 5/2002 |
| CN | 1535126 A | 10/2004 |
| DE | 2826383 | 12/1979 |
| DE | 3304230 | 8/1984 |
| DE | 8807746 | 11/1988 |
| DE | 3837248 | 5/1990 |
| DE | 3841503 | 6/1990 |
| DE | 9102407 | 7/1991 |
| DE | 3719561 | 1/1998 |
| DE | 19803460 | 8/1999 |
| DE | 19944401 | 3/2001 |
| DE | 10112289 | 8/2001 |
| DE | 10140715 | 3/2002 |
| DE | 10120787 | 1/2003 |
| EP | 0000593 | 2/1979 |
| EP | 0142671 | 5/1985 |
| EP | 0172490 | 2/1986 |
| EP | 0297360 | 1/1989 |
| EP | 0320320 | 6/1989 |
| EP | 0324120 | 7/1989 |
| EP | 0413025 | 2/1991 |
| EP | 0458576 | 11/1991 |
| EP | 0563953 | 10/1993 |
| EP | 0565331 | 10/1993 |
| EP | 0575274 | 12/1993 |
| EP | 0593375 | 4/1994 |
| EP | 0598984 | 6/1994 |
| EP | 0709941 | 5/1996 |
| EP | 0724894 | 8/1996 |
| EP | 0726083 | 8/1996 |
| EP | 0736308 | 10/1996 |
| EP | 0743029 | 11/1996 |
| EP | 0755698 | 1/1997 |
| EP | 0763371 | 3/1997 |
| EP | 0765673 | 4/1997 |
| EP | 0765674 | 4/1997 |
| EP | 0783904 | 7/1997 |
| EP | 0884066 | 12/1998 |
| EP | 0885629 | 12/1998 |
| EP | 0920840 | 6/1999 |
| EP | 0927544 | 7/1999 |
| EP | 1031414 | 8/2000 |
| EP | 1038505 | 9/2000 |
| EP | 1057455 | 12/2000 |
| EP | 1072402 | 1/2001 |
| EP | 1075854 | 2/2001 |
| EP | 1138269 | 4/2001 |
| EP | 1138349 | 10/2001 |
| EP | 1147785 | 10/2001 |
| EP | 1219258 | 7/2002 |
| EP | 1226787 | 7/2002 |
| EP | 1238683 | 9/2002 |
| EP | 1250893 | 10/2002 |
| EP | 1057454 | 11/2003 |
| EP | 1457234 | 9/2004 |
| EP | 1495735 | 1/2005 |
| EP | 1512373 | 3/2005 |
| EP | 1535582 | 6/2005 |
| EP | 1627662 | 2/2006 |
| EP | 1650615 | 4/2006 |
| EP | 1797836 | 6/2007 |
| EP | 1839705 | 10/2007 |
| EP | 1854505 | 11/2007 |

(56) References Cited

FOREIGN PATENT DOCUMENTS

| | | |
|---|---|---|
| FR | 2199453 | 4/1974 |
| FR | 2591902 | 6/1987 |
| GB | 1251424 | 10/1971 |
| GB | 1274017 | 5/1972 |
| GB | 1546625 | 5/1979 |
| GB | 2044908 | 10/1980 |
| GB | 2059053 | 4/1981 |
| GB | 2059054 | 4/1981 |
| GB | 2123287 | 2/1984 |
| GB | 2212010 | 7/1989 |
| GB | 2239675 | 7/1991 |
| GB | 2270159 | 3/1994 |
| GB | 2356570 | 5/2001 |
| GB | 2360461 | 9/2001 |
| GB | 2360946 | 10/2001 |
| GB | 2364376 | 1/2002 |
| GB | 2368020 | 4/2002 |
| GB | 2390021 | 12/2003 |
| GB | 2397528 | 7/2004 |
| JP | S54129791 A | 10/1979 |
| JP | S5552766 A | 4/1980 |
| JP | S5577187 A | 6/1980 |
| JP | S574007 A | 1/1982 |
| JP | S62165985 A | 7/1987 |
| JP | S6323648 A | 1/1988 |
| JP | S63249577 A | 10/1988 |
| JP | S6427554 A | 1/1989 |
| JP | H0366387 A | 3/1989 |
| JP | S6481222 A | 3/1989 |
| JP | H01181877 A | 7/1989 |
| JP | H02199 | 1/1990 |
| JP | H022199 A | 1/1990 |
| JP | H0213014 U | 1/1990 |
| JP | H0285694 | 3/1990 |
| JP | H02174804 A | 7/1990 |
| JP | H02285694 A | 11/1990 |
| JP | H0319385 A | 1/1991 |
| JP | H0316956 U | 2/1991 |
| JP | H03183184 A | 8/1991 |
| JP | H03281390 | 12/1991 |
| JP | H0622871 A | 2/1994 |
| JP | H06154239 A | 6/1994 |
| JP | H079179 A | 1/1995 |
| JP | H0763957 A | 3/1995 |
| JP | H07328025 A | 12/1995 |
| JP | H0815539 A | 1/1996 |
| JP | H0854538 A | 2/1996 |
| JP | H0984803 A | 3/1997 |
| JP | H09141869 A | 6/1997 |
| JP | H09220292 A | 8/1997 |
| JP | H1014661 A | 1/1998 |
| JP | H0199574 A | 4/1998 |
| JP | H1147146 A | 2/1999 |
| JP | H11232229 A | 5/1999 |
| JP | 2000037400 A | 2/2000 |
| JP | 2000153003 A | 6/2000 |
| JP | 2000300684 A | 10/2000 |
| JP | 2001000560 A | 1/2001 |
| JP | 2001029124 A | 2/2001 |
| JP | 2001145520 A | 5/2001 |
| JP | 2001196665 A | 7/2001 |
| JP | 2001343560 A | 12/2001 |
| JP | 2002272861 A | 9/2002 |
| JP | 2003052843 A | 2/2003 |
| JP | 2005017796 A | 1/2005 |
| JP | 2005027702 A | 2/2005 |
| JP | 2006192073 A | 7/2006 |
| RU | 2082337 | 6/1997 |
| RU | 2089126 | 9/1997 |
| RU | 2089127 | 9/1997 |
| RU | 2096051 | 11/1997 |
| RU | 2122848 | 12/1998 |
| WO | WO 1986002783 | 5/1986 |
| WO | WO 1988004592 | 6/1988 |
| WO | WO 1990000420 | 1/1990 |
| WO | WO 1990006727 | 6/1990 |
| WO | WO 1990012548 | 11/1990 |
| WO | WO 1991001053 | 1/1991 |
| WO | WO 1991002562 | 3/1991 |
| WO | WO 1991012050 | 8/1991 |
| WO | WO 1991013652 | 9/1991 |
| WO | WO 1991013653 | 9/1991 |
| WO | WO 1991018646 | 12/1991 |
| WO | WO 1992016338 | 1/1992 |
| WO | WO 1992003977 | 3/1992 |
| WO | WO 1992006739 | 4/1992 |
| WO | WO 1992019165 | 11/1992 |
| WO | WO 1993005920 | 4/1993 |
| WO | WO 1993021843 | 11/1993 |
| WO | WO 1995003089 | 2/1995 |
| WO | WO 1995004393 | 2/1995 |
| WO | WO 1995010243 | 4/1995 |
| WO | WO 1995014251 | 5/1995 |
| WO | WO 1995015725 | 6/1995 |
| WO | WO 1995032441 | 11/1995 |
| WO | WO 1995033518 | 12/1995 |
| WO | WO 1996009853 | 4/1996 |
| WO | WO 1996018347 | 6/1996 |
| WO | WO 1996022741 | 8/1996 |
| WO | WO 1996022813 | 8/1996 |
| WO | WO 1996023447 | 8/1996 |
| WO | WO 1996024182 | 8/1996 |
| WO | WO 1996024406 | 8/1996 |
| WO | WO 1996025979 | 8/1996 |
| WO | WO 1996028212 | 9/1996 |
| WO | WO 1996034316 | 10/1996 |
| WO | WO 1996036396 | 11/1996 |
| WO | WO 1996039734 | 12/1996 |
| WO | WO 1996041579 | 12/1996 |
| WO | WO 1997000777 | 1/1997 |
| WO | WO 1997013458 | 4/1997 |
| WO | WO 1997013552 | 4/1997 |
| WO | WO 1997022384 | 6/1997 |
| WO | WO 1997028752 | 8/1997 |
| WO | WO 1997037602 | 10/1997 |
| WO | WO 1997037723 | 10/1997 |
| WO | WO 1998004317 | 2/1998 |
| WO | WO 1998005286 | 2/1998 |
| WO | WO 1998005380 | 2/1998 |
| WO | WO 1998006456 | 2/1998 |
| WO | WO 1998007379 | 2/1998 |
| WO | WO 1998020937 | 5/1998 |
| WO | WO 1998024507 | 6/1998 |
| WO | WO 1998029134 | 7/1998 |
| WO | WO 1998041158 | 9/1998 |
| WO | WO 1998051235 | 11/1998 |
| WO | WO 1998052481 | 11/1998 |
| WO | WO 1998058595 | 12/1998 |
| WO | WO 1999010046 | 3/1999 |
| WO | WO 1999017666 | 4/1999 |
| WO | WO 1999017667 | 4/1999 |
| WO | WO 1999017668 | 4/1999 |
| WO | WO 1999027997 | 6/1999 |
| WO | WO 1999029243 | 6/1999 |
| WO | WO 1999034867 | 7/1999 |
| WO | WO 1999038569 | 8/1999 |
| WO | WO 1999039410 | 8/1999 |
| WO | WO 1999043387 | 9/1999 |
| WO | WO 1999044638 | 9/1999 |
| WO | WO 1999046005 | 9/1999 |
| WO | WO 1999049937 | 10/1999 |
| WO | WO 1999058195 | 11/1999 |
| WO | WO 1999062472 | 12/1999 |
| WO | WO 1999066988 | 12/1999 |
| WO | WO 2000002491 | 1/2000 |
| WO | WO 2000003257 | 1/2000 |
| WO | WO 2000007514 | 2/2000 |
| WO | WO 2000030714 | 6/2000 |
| WO | WO 2000032272 | 6/2000 |
| WO | WO 2000040266 | 7/2000 |
| WO | WO 2000041278 | 7/2000 |
| WO | WO 2000043070 | 7/2000 |
| WO | WO 2000044294 | 8/2000 |
| WO | WO 2000053113 | 9/2000 |

(56) References Cited

FOREIGN PATENT DOCUMENTS

| | | |
|---|---|---|
| WO | WO 2000054649 | 9/2000 |
| WO | WO 2000054685 | 9/2000 |
| WO | WO 2000062700 | 10/2000 |
| WO | WO 2000064537 | 11/2000 |
| WO | WO 2000066226 | 11/2000 |
| WO | WO 2000071045 | 11/2000 |
| WO | WO 2000074583 | 12/2000 |
| WO | WO 2000074781 | 12/2000 |
| WO | WO 2000078242 | 12/2000 |
| WO | WO 2001014012 | 3/2001 |
| WO | WO 2001026573 | 4/2001 |
| WO | WO 2001034048 | 5/2001 |
| WO | WO 2001042671 | 6/2001 |
| WO | WO 2001054606 | 8/2001 |
| WO | WO 2001054770 | 8/2001 |
| WO | WO 2001078830 | 10/2001 |
| WO | WO 2002009813 | 2/2002 |
| WO | WO 2002026147 | 4/2002 |
| WO | WO 2001003257 | 7/2002 |
| WO | WO 2002053050 | 7/2002 |
| WO | WO 2002069825 | 9/2002 |
| WO | WO 2002078559 | 10/2002 |
| WO | WO 2002094116 | 11/2002 |
| WO | WO 2003005883 | 1/2003 |
| WO | WO 2003049633 | 6/2003 |
| WO | WO 2003103529 | 12/2003 |
| WO | WO 2004000150 | 12/2003 |
| WO | WO 2004011848 | 2/2004 |
| WO | WO 2004033040 | 4/2004 |
| WO | WO 2004037068 | 5/2004 |
| WO | WO 2004037287 | 5/2004 |
| WO | WO 2004073537 | 9/2004 |
| WO | WO 2004080279 | 9/2004 |
| WO | WO 2004084752 | 10/2004 |
| WO | WO 2004086947 | 10/2004 |
| WO | WO 2005007003 | 1/2005 |
| WO | WO 2005009266 | 2/2005 |
| WO | WO 2005030317 | 4/2005 |
| WO | WO 2005046793 | 5/2005 |
| WO | WO 2005065288 | 7/2005 |
| WO | WO 2005092438 | 10/2005 |
| WO | WO 2005096981 | 10/2005 |
| WO | WO 2005099369 | 10/2005 |
| WO | WO 2005112815 | 12/2005 |
| WO | WO 2006006123 | 1/2006 |
| WO | WO 2006036968 | 4/2006 |
| WO | WO 2006066226 | 6/2006 |
| WO | WO 2006089227 | 8/2006 |
| WO | WO 2006101735 | 9/2006 |
| WO | WO 2006116141 | 11/2006 |
| WO | WO 2007035444 | 3/2007 |
| WO | WO 2007122611 | 11/2007 |
| WO | WO 2008007218 | 1/2008 |
| WO | WO 2008070747 | 6/2008 |
| WO | WO 2008153999 | 12/2008 |
| WO | WO 2010102255 | 9/2010 |
| WO | WO 2012023129 | 2/2012 |

OTHER PUBLICATIONS

[No Author] Webpage www.gallery.com—Rutile (Titanium Oxide)—Retrieved Oct. 3, 2011 from Http://www.galleries.com/minerals/oxides/rutile/rutile.htm. 2 pages.

[No Author] Altea Therapeutics—Medicines Made Better (single page website print-out, retrieved Sep. 30, 2004, © 2003-2004).

[No Author] Energy Systems Coropration, "A Practical Guide for the PhotoDern.RTM.VL user," Haifa, Israel, Commercial Brochure 8 Pages, Oct. 1995.

[No Author] "Final Report on the LFDL-10 Laser System for the GCA Corporation," Candela Corp., Natick, MA, Section II, subsection 5, pp. 13-15 & 27, Mar. 1982.

[No Author] "Fractional Photothermolysis Redefines Facial Skin Regeneration Science," Aesthetic Buyers Guide, Mar./Apr. 2004, www.miinews.com, pp. 1-4.

[No Author] "Hydrogel Dressings Contain Particles During Laser Therapy," Dermatology Times, ISSN-01966197, p. 26 (1994).

[No Author] "Instruction Manual, TFDL-10," Adapted for SLAC, Candela Corporation, Natick, Oct. 1985.

[No Author] "Lasers Battle for Prostatectomy Market," Medical Laser Industry Report, 5:1-3 (Aug. 1991).

[No Author] "LFDL-8 Instruction Manual," Candela Laser Corporation, Wayland, MA Revised Oct. 1987.

[No Author] "LFDL-8 Instruction Manual," Candela Laser Corporation, Wayland, MA, Jan. 1982, Revised Jun. 1987.

[No Author] "LFDL-8 Instruction Manual," Cynosure, Inc., Bedford, MA, Revised Nov. 1992.

[No Author] "Prostate Enlargement: Benigh Prostatic Hyperplasia," brochure from U.S. Department of Health and Human Services, pp. 1-14, (at least by 1992).

[No Author] "Special Instruction and Test Results for the LFDL-2 Wave Guide Laser," Candela Laser Corporation, Wayland, MA, Sep. 1982.

[No Author] "The Laser TURP Advantage," Intra-Sonix, Inc. pp. 1-4 (1991).

[No Author] Beckman Laser Institute "Experimental PDT to Prevent Esophegus Cancer," (8 Pages) 1996.

[No Author] Cynosure Dioderm 510(k) Notification K992765 for Cynosure, Inc. to Food and Drug Administration, dated: Aug. 16, 1999 and Aug. 20, 1999 (Additional Information).

[No Author] Reliant Technologies, Inc. "Physicians Guide: Understanding Faxel Laser Treatment," pp. 1-10 (2004).

[No Author] Ritter Sybron Corporation, "Electrosurgery, A Guide for Operating Room Personnel," pp. 1-22, (Jun. 1976).

[No Author] Selective Photothermolysis of Sebaceous Glands, Department of Health and Human Services, Public Health Service, Small Business Innovation Research Program II Grant Application, Cynosure, Inc., dated: Jul. 27, 2000, pp. 17-39 and 43-44.

[No Author] "Innovative Non-Surgical Treatment for Barrett's Esophagus", Jul. 1995, see http://www.plsgroup.com/dg950728.htm.

"American Society for Laser Medicine and Surgery Abstracts," Lasers in Surgery and Medicine, Supplement 6, p. 46 (1994).

Anderson, R.R., et al., "Microvasculature Can Be Selectively Damaged Using Dye Lasers: A Basic Theory and Experimental Evidence in Human Skin," Lasers in Surgery and Medicine 1:263-276 (1981).

Altshuler et al., "Human Tooth as an Optical Device," SPIE vol. 1429 Holography and Interferometry and Optical Pattern Recognition in Biomedicine, pp. 95-104, 1991.

Altshuler et al., "Modern Optics and Dentistry," Laser in Dentistry, pp. 283-297, 1995.

Altshuler et al., "New Optical Effects in the Human Hard Tooth Tissues," Lasers and Medicine, Proc. SPIE vol. 1353, pp. 97-102, 1989.

Altshuler, et al., "Self Canalization of Laser Microbeam in Tissue as Fundamental Mechanism of Fractional Skin Resurfacing", Lasers in Surgery and Medicine Supple 15, 21, 2003.

Altshuler, G.B. et al., "Acoustic response of hard dental tissues to pulsed laser action," SPIE, vol. 2080, Dental Application of Lasers, pp. 97-103, 1993.

Altshuler, G.B. et al., "Extended theory of selective photothermolysis," Lasers in Surgery and Medicine, vol. 29, pp. 416-432, 2001.

Amy, R.L. et al., "Selective mitochondrial damage by a ruby laser microbeam: An electron microscopic study," Science, vol. 15, pp. 756-758, Nov. 1965.

Anderson, R.R. et al., "Selective photothermolysis: Precise microsurgery by selective absorption of pulsed radiation," Science, vol. 220, pp. 524-527, Apr. 1983.

Anderson, R.R. et al., "The optics of human skin," Journal of Investigative Dermatology, vol. 77, No. 1, pp. 13-19, 1981.

Ang et al., "Kalman Filtering for Real-Time Orientation Tracking of Handheld . . . ", 2004 IEEE/RSJ Iner Conf on Intell Robots and Systems (IROS), Sendai, Japan.

Ang et al., "Design of All-Accelerometer Inertial Measurement Unit for Tremor Sensing in Hand-Held . . . ", 2003 IEEE Inter Conf on Robotice and Automation (col. 2), Taipei, Taiwan.

(56) References Cited

OTHER PUBLICATIONS

Angelis, et al., "Fractional, Non-Ablative Laser Therapy for the Treatment of Striae Distensae", White Paper published by Palomar Medical Technologies, Inc. (2009)5 pages.
Apfelberg et al. "Analysis of Complications of Argon Laser Treatment for Port Wine Hemangiomas with Reference to Striped Technique," Lasers in Surgery and Medicine, 2:357-371 (1983).
Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).
Apfelberg, D.B., "A Preliminary Study of the Combined Effect of Neodymium:YAG Laser Photocoagulation and Direct Steroid Instillation in the Treatment of Capillary/Cavernous Hemangiomas of Infancy," Department of Plastic Surgery and Comprehensive Laser Center, Palo Alto Medical Foundation, Palo Alto, CA, pp. 94-103 (1989).
Apfelberg, D.B., "Combination Treatment for Massive Cavernous Hemangioma of the Face: YAG Laser Photocoagulation Pulse Direct Steroid Injection Followed by YAG Laser Resection with Sapphire Scalpel Tips, Aided by Superspective Embolization," Lasers in Surgery and Medicine, 10:217-223 (1990).
Belikov, A.V. et al., "Identification of enamel and dentine under tooth laser treatment," SPIE vol. 2623, Progress in Biomedical Optics Europt Series, Proceedings of Medical Applications of Lasers III, pp. 109-116, Sep. 1995.
Benjavitvilai, C. et al., "Fuzzy Calibration of Magnetometer in Presence of Surgical Microscope," 2005 27th Annual International Conference of the IEEE Engineering in Medicine and Biology Society (IEEE Cat. No. 05CH37611C), Shanghai, China, Aug. 31-Sep. 3, 2005.
Bjerring, P. et al., "Selective Non-Ablative Wrinkle Reduction by Laser," J Cutan Laser Ther, vol. 2, pp. 9-15, 2000.
Blankenau et al., "In Vivo Caries-Like Lesion Prevention with Argon Laser: Pilot Study," Journal of Clinical Laser Medicine and Surgery, vol. 17, No. 6, pp. 241-243, 1999.
Bogdan Allemann, et al., "Laser Principles", Physical and Electronic Properties of Lasers, Basics in Dermatological Laser Applications, Curr. Probl. Dermatol, Basel, Karger. Zurich, Switzerland and Miami, Florida. vol. 42, pp. 7-23, 2011, 17 pages.
Bohm et al., "The Pilosebaceous Unit is Part of the Skin Immune System," Dermatology, 196:75-79, 1998.
Boiteux, M., et al., "A Transverse Flow Repetitive Dye Laser," Applied Optics, 9, 514 (1970).
Boulnois, J., "Photophysical Processes in Recent Medical Laser Developments: a Review," Lasers in Medical Science, vol. 1:47-66 (1986).
Brauer, Jeremy A. et al., "Successful and Rapid Treatment of Blue and Green Tattoo Pigment With a Novel Picosecond Laser", Archives of Dermatology, vol. 148, No. 7, 2012, pp. 820-823.
Britt et al., "The Effect of pH or Photobleaching of Organic Laser Dyes", IEEE J. Quantum Electron. (Dec. 1972), 913-914.
Burlamacchi et al, "A Simple Reliable Waveguide Dye Laser for Ophthalmological Applications," Rev of Sci Instrum; vol. 46; No. 3; pp. 281-283, Mar. 1975.
Chan, E.K., "Effects of Compression on Soft Tissue Optical Properties," IEEE Journal of Selected Topics in Quantum Electronics, vol. 2, No. 4, pp. 943-950 (Dec. 1996).
Costello, A. et al., "Nd:YAG Laser Ablation of the Prostate as a Treatment for Benign Prostatic Hypertrophy," Lasers in Surgery and Medicine, 12:121-124 (1992).
Cunliffe, "Acne Vulgaris. The Past, the Present and the Future," Acta Bermatovener (Stockh) Suppl. 120, pp. 34-38, 1985.
Dabrowska, "Intravital Treatment of the Pulp with Stimulation Laser Biostimulation," Abstract Rocz-Akad-Med-Bialymst. 1997; 42(1): 168-76.
Dierickx, C.C. et al., "Thermal Relaxation of Port-wine Stain Vessels Probed In Vivo: The Need for 1-10 Millisecond Laser Pulse Treatment," The Journal for Investigative Dermatology, pp. 709-714 (1995).
Dixon et al. "Hypertrophic Scarring in Argon Laser Treatment of Port-Wine Stains," Plastic and Reconstructive Surgery, 73:771-777 (1984).
Dock et al., "Clinical Histologic and Ultrastructural Evaluation of Solar Elastosis Treated With the Pulsed Dye Laser," American Society for Laser Medicine and Surgery Abstracts, p. 54 (Apr. 1997).
Doukas et al., "Transdermal Drug Delivery With a Pressure Wave," Advanced Drug Delivery Reviews 56 (2004), pp. 559-579.
Dover J.S. et al., "Pigmented guinea pig skin irradiated with Q-switched ruby laser pulses," Arch Dermatol, vol. 125, pp. 43-49, Jan. 1989.
Dufresne et al., "Squamous cell carcinoma arising from the follicular occlusion triad," J. Am. Acad. Dermatol. 35(3), Part 1:475-477, 1996.
Ellenberger, et al. "Single-Frequency Nd:Glass Laser Oscillator with Pulse-Transmission-Mode Q-Switch with Pulse-Transmission-Mode Q-Switch," Optics communication, vol. 81, No. 6 (Mar. 1991).
Ertan et al., "Esophagel Adenocarcinoma Associated with Barrett's Esophagus: Long-term Management with Laser Ablation", Am. J. Gastro, 90: pp. 2201-2203, 1995.
Fallon Friedlander, "Effective Treatment of Acne Fulminans-Associated Granulation Tissue with the Pulsed Dye Laser," Pediatric Dermatology, 15(5):396-398, 1998.
Finkelstein L.H. et al., "Epilation of hair-bearing urethral grafts using the neodymium:yag surgical laser," Journal of Urology, vol. 146, pp. 840-842, Sep. 1991.
Fiskerstrand E.J. et al., "Hair Removal with Long Pulsed Diode Lasers: A Comparison Between Two Systems with Different Pulse Structures," Lasers in Surgery and Medicine, vol. 32, pp. 399-404, 2003.
Fletcher, A.N. et al., "Improving the Output and Lifetime of Flashlamp-Pumped Dye Lasers" Proceedings of the International Conference on Lasers '85, pp. 797-804, Dec. 2-6, 1985.
Forrest-Winchester et al., "The Effect of Infrared Laser Radiation on Dentinal Permeability in vitro," Department of Dentistry, University of Queensland Dental School, pp. 1-8, 1992.
Friedman-Birnbaum et al., "Seborrheic Skin and Acne Vulgaris as Protective Factors against the Development of Basal Cell Epithelioma," Dermatolgica, 183:160-163, 1991.
Furumoto, H., "Dye Chemistry and System Study for Optimum Laser Operation at 436 NM Using the LFDL-10 Laser," Prepared for Burlington Division Geophysical Corporation of America, pp. 1-23, Mar. 1982.
Ginsbach et al. "New Aspects in the Management of Benign Cutaneous Tumors," Laser 79 Opto-Electronics, Munich Conference Proceedings, 344-347 (1979).
Goldberg, "Lasers for Facial Rejuvenation", Am J. Clin. Dermatol., 4(4):225-234, 2003, 10 pages.
Goldberg, "Nonablative Resurfacing", Clinics in Plastic Surgery, Skin Laser and Surgery Specialists of New York and New Jersey. Westwood, New Jersey. vol. 27, No. 2, Apr. 2000, 6 pages.
Goldman, L. et al. "Treatment of basal cell epithelioma by laser radiation," JAMA, vol. 189, No. 10, pp. 773-775, 1964.
Goldman, L. et al., "Effect of the laser beam on the skin, III. Exposure of cytological preparations," Journal of Investigative Dermatology, vol. 42, pp. 247-251, 1964.
Goldman, L. et al., "Effect of the laser beam on the skin, Preliminary report" Journal of Investigative Dermatology, vol. 40, pp. 121-122, 1963.
Goldman, L. et al., "Impact of the laser on nevi and melanomas," Archives of Dermatology, vol. 90, pp. 71-75, Jul. 1964.
Goldman, L. et al., "Laser action at the cellular level," JAMA, vol. 198, No. 6, pp. 641-644, Nov. 1966.
Goldman, L. et al., "Laser treatment of tattoos, A preliminary survey of three year's clinical experience," JAMA, vol. 201, No. 11, pp. 841-844, Sep. 1967.
Goldman, L. et al., "Long-term laser exposure of a senile freckle," ArchEnviron Health, vol. 22, pp. 401-403, Mar. 1971.
Goldman, L. et al., "Pathology, Pathology of the effect of the laser beam on the skin," Nature, vol. 197, No. 4870, pp. 912-914, Mar. 1963.

(56) References Cited

OTHER PUBLICATIONS

Goldman, L. et al., "Preliminary investigation of fat embolization from pulsed ruby laser impacts of bone," Nature, vol. 221, pp. 361-363, Jan. 1969.
Goldman, L. et al., "Radiation from a Q-switched ruby laser, EffeCt of repeated impacts of power output of 10 megawatts on a tattoo of man," Journal of Investigative Dermatology, vol. 44, pp. 69-71, 1965.
Goldman, L. et al., "Replica microscopy and scanning electron microscopy of laser impacts on the skin," Journal of Investigative Dermatology, vol. 52, No. 1, pp. 18-24, 1969.
Goldman, L. et al., "The biomedical aspects of lasers," JAMA, vol. 188, No. 3, pp. 302-306, Apr. 1964.
Goldman, L. et al., "The effect of repeated exposures to laser beams," Acta derm.-vernereol., vol. 44, pp. 264-268, 1964.
Goldman, L., "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.
Goldman, L., "Effects of new laser systems on the skin," Arch Dermatol., vol. 108, pp. 385-390, Sep. 1973.
Goldman, L., "Laser surgery for skin cancer," New York State Journal of Medicine, pp. 1897-1900, Oct. 1977.
Goldman, L., "Surgery by laser for malignant melanoma," J. Dermatol. Surg. Oncol., vol. 5, No. 2, pp. 141-144, Feb. 1979.
Goldman, L. "The skin," Arch Environ Health, vol. 18, pp. 434-436, Mar. 1969.
Goldman, L., Biomedical Aspects of the Laser, Springer-Verlag New York Inc., publishers, Chapts. 1, 2 & 23, 1967.
Goldman, M. P., "Leg Veins and Lasers," American Society for Laser Medicine and Surgery Abstracts, Fourteen Annual Meeting, Toronto, Ontario, Canada, p. 48 (Apr. 8-10, 1994).
Goldman, M.P., "Sclerotherapy—Treatment of Varicose and Telangiectatic Leg Veins," Second Edition, Mosby, pp. 454-467 (1995).
Gottlieb, I., "Power Supplies, Switching Regulators, Inverters & Converters," 1976.
Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).
Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.
Grossman, M.C. et al., "Damage to hair follicles by normal-mode ruby laser pulses," Journal of he American Academy of Dermatology, vol. 35, No. 6, pp. 889-894, Dec. 1996.
Grossman, M.C. et al., "Laser Targeted at Hair Follicles, " Lasers Med Surg., Suppl. 13:221 (2001).
Habbema, Louis et al., "Minimally invasive non-thermal laser technology using laser-induced optical breakdown fir skin rejuvenation", J. Biophotonics, vol. 5, No. 2, 2012, pp. 194-199.
Haedersal, et el., "Fractional Nonablative 1540 nm Laser Resurfacing for Thermal Burn Scars: A Randomized Controlled Trial", Lasers in Surgery and Medicine, 41:189-195, 2009, 7 pages.
Hicks et al., "After Low Fluence Argon Laser and Flouride Treatment," Compendium, vol. 18, No. 6, Jun. 1997.
Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.
Hsu et al., "Combined Effects of Laser Irradiation/Solution Flouride Ion on Enamel Demineralization," Journal of Clinical Laser Medicine and Surgery, vol. 16, No. 2 pp. 93-105, 1998.
Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).

Hulsbergen Henning et al., "Port Wine Stain Coagulation Experiments with a 540-nm Continuous Wave Dye-Laser," Lasers in Surgery and Medicine, 2:205-210 (1983).
Invention description to certificate of authorship, No. 719439, "The ring resonator of optical quantum generator" (Aug. 15, 1975).
Invention description to certificate of authorship, No. 741747, "The modulator of optical radiation intensity" (Oct. 10, 1977).
Invention description to certificate of authorship, No. SU 1257475 A1, "Laser interferometric device to determine No. linearity of an index of refraction of optical medium" (Sep. 15, 1986).
Invention description to certificate of authorship, No. SU 1326962 A1, "The way of determination of non-linearity of an index of refraction of optical medium" (Jul. 30, 1987).
Invention description to certificate of autorship, No. 532304, "The way of investigation of radiation time structure of optical quantum generator" (Jul. 9, 1974).
Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).
Johnsson et al., "No photoinactivation of Propionibacterium acnes with soft laser treatment," Dermatologica, 175(1):50, 1987.
Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.
Kandel, Laurence B., M.D., et al., "Transurethral Laser Prostatectomy in the Canine Model," Lasers in Surgery and Medicine, 12:33-42 (1992).
Kantor et al., "Treatment of acne keloidalis nuchae with carbon dioxide laser," J. Am. Acad. Dermatol., 14:263-267, 1986.
Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.
Karu, "Photobiological Fundamentals of Low-Power Laser Therapy," 8th Congress of International Society for Laser Surgery and Medicine, Mar. 30, 1987.
Kazmina et al., "Laser Prophlaxis and Treatment of Primary caries," SPIE vol. 1984, pp. 231-233.
Kelly et al., "Nonablative Laser Treatment of Facial Rhytides: United States Phase II Clinical Study," American Society for Laser Medicine and Surgery Abstracts, 10(33):38 (1998).
Kilmer et al., "Pulse Dye Laser Treatment of Rhytids," American Society for Laser Medicine and Surgery Abstracts, p. 44 (Apr. 1997).
Klein, E. et al., "Biological effects of laser radiation 1.," Northeast Electroncis Research and Engineering Meeting, NEREM Record, IEEE catalogue No. F-60, pp. 108-109, 1965.
Kliewer, Michael L. et al., "Excited State Absorption of Pump Radiation as a Loss Mechanism in Solid-State Lasers", IEEE Journal of Quantum Electronics, vol. 25, 1989, pp. 1850-1854.
Korobov et al., "Dependence of the Quantum Yield of Intercombinational Conversion into the Triplet State of Rhodamine 6G on the pH of the Medium", Zhur. Prikl. Spektrosk. 24(1) 28-31 (Jan. 1976).
Kozlov et al., "Laser in Diagnostics and Treatment of Microcirculation Disorders Under Parodontitis," SPIE vol. 1984, pp. 253-264.
Krames et al. "Status and Future of High-Power Light-Emitting Diodes for Solid State Lighting", J. Display Technol., 3(2):160-175 (Jun. 2007).
Kuhns, J.G. et al., "Biological effects of laser radiation II Effects of laser irradiation on the skin," NEREM Record, pp. 152-153, 1965.
Kuhns J.G. et al., "Laser injury in skin," Laboratory Investigation, vol. 17, No. 1, pp. 1-13, Jul. 1967.
Kuizenga, Dirk J. et al., "FM and AM Mode Locing of the Homogenous Laser—Part I: Theory", IEEE Journal of Quantum Electronics, vo. 6, No. 11, Nov. 1970, pp. 694-708.
Lee, Junsu et al., "Q-switched Mode-Locking of an Erbium-doped Fiber Laser through Subharmonic Cavity Modulation", Photonics Conference (IPC), 202 IEEE, Sep. 23, 2012, pp. 664-665.
Leger, J. et al., "Geometrical Transformation of Linear Diode-Laser Arrays for Longitudinal Pumping of Solid-State Lasers", IEEE Journal of Quantum Electronics, vol. 28, No. 4, Apr. 1992.

(56) References Cited

OTHER PUBLICATIONS

Lesnik et al., "Agents that cause enlargement of sebaceous glands in hairless mice," Arch. Dermatol., 284:100-105, 1992.
Levin, G. et al., "Designing with hyseretic current-mode control," EDN Magazine, pp. 1-8, Apr. 11, 1996.
Levin, G. et al., "Designing with hyseretic current-mode control," EDN Magazine, pp. 1-8, Apr. 28, 1994.
Lucchina et al., "Fluorescence photography in the evaluation of acne," J. Am. Acad. Dermatol. 35:58-63 (1996).
Maegawa, et al., "Effects of Near-Infrared Low-Level Laser Irradiation on Microcirculation," Lasers in Surgery and Medicine, vol. 27, pp. 427-437, 2000.
Mamedova et al., "Microbiological Estimate of Parodontis Laser Therapy Efficiency," SPIE vol. 1984, pp. 247-249.
Mang, "Effect of Soft Laser Treatment on Wound Healing in the Hamster Oral Mucosa," Lasers in Surgery and Medicine, Supp. 8, Abstracts, Abstract 25, 1996.
Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.
Manstein, D., et al., "Fractional Photothermolysis: A New Concept for Cutaneous Remodeling Using Microscopic Patterns of Thermal Injury," Lasers in Surgery and Medicine, 34: 426-438 (2004).
Manuskiatti et al., "Laser hair removal affects sebaceous glands and sebum excretion . . . ," J. Am. Acad. Dermatol., 41:176-180, 1999.
Margolis, R.J. et al., "Visible action spectrum for melanin-specific selective photothermolysis," Lasers in Surgery and Medicine, vol. 9, pp. 389-397, 1989.
Marinelli et al., "Diode laser illuminated automotive lamp systems," SPIE Proceedings vol. 3285:170-177 (1998).
Marshak, I.S., et al., "Pulsed Light Sources," State Power Engineering Press, Moscow and Leningrad (1963).
Matsunaga et al., "Effect of pH on Dye-Laser Output Power", J. Appl. Phys. 48(2):842-844 (Feb. 1977).
McCullough, David L., M.D., "Transurethral Laser Treatment of Benign Prostatic Hyperplasia," and "Transurethral Ultrasound-guided Laser-Induced Prostatectomy (TULIP) Procedure): A Canine Prostate Feasibility Study," by Roth, Robert A., M.D., et al., The Journal of Urology, 146:1126-1135 (1991).
McDaniel, et al., "Hexascan: A New Robotized Scanning Laser Handpiece," Cutis, 45:300-305 (1990).
McNicholas, T. A., et al., "Interstitial Laser Coagulation of the Prostate: Experimental Studies," SPIE, 1421:30-35 (1991). (From Proceedings of Lasers in Urol., Laparoscopy, and General Surgery, Jan. 21-23, 1991).
Mingxin, Qiu et al., "Performance of a Nd:YVO4 microchip laser with continuous-wave pumping at wavelengths between 741 and 825 nm", Applied Optics, vol. 32, No. 12, Apr. 20, 1993, p. 2085.
Moretti, Michael, "Holmium Boosts Orthopedic Laser Development," Medical Laser Buyers Guide, p. 93 (1992).
Moretti, Michael, "Lasers Improve Prostatectomy Treatment," Medical Laser Buyers Guide, p. 94-96 (1992).
Mostovnikov, V.A. et al., "Recovery of Lasing Properties of Dye Solutions after Their Photolysis," Sov. J. Quantum Electron, 6(9), Sep. 1976, pp. 1126-1128.
Nanni, C.A. et al., "Complications of Carbon Dioxide Laser Resurfacing," Washington Inst. of Dermatol. Surg. 24:315-320 (1998).
Nemeth, et al., "Copper vapor laser treatment of pigmented lesions," Lasers Surg. Med. Supp. 2:51 (1990).
Ogiso et al, "Phase Transitions of Rat Stratum Corneum Lipids by an Electron Paramagnetic Resonance Study and Relationship of Phase States to Drug Penetration," Biochimica et Biophysica Acta 1301:97-104 (1996).
Ohbayashi, "Stimulatory Effect of Laser Irradiation on Calcified Nodule Formation in Human Dental Pulp Fibroblasts," Abstract J-Endod. Jan. 1999; 25(1): 30-3.
Ohshiro et al., "The Ruby and Argon Lasers in the Treatment of the Naevi," Annals Academy of Medicine, Apr. 1983, vol. 12, No. 2, pp. 388-395.
Oleinik, et al., "Automatized Securing Definition for Laser Therapy Indications in Case of Non-complicated Caries," SPIE, vol. 1984, pp. 238-244.
Oraevsky, Alexander A. et al., "Plasma Mediated Ablation of Biological Tissues with Nanosecond-to-Femtosecond Laser Pulses: Relative Role of Lineear and Nonlinear Absorption", IEEE Journal of Selected Topics in Quantum Electronics, vol. 2, No. 4, Dec. 1996, pp. 801-809.
Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.
Overholt BF et al. "Balloon photodynamic therapy of esophageal cancer: effect of increasing balloon size." PubMed; Lasers Surg Med. 1996, 18(3):248-52.
Ozawa et al., "Stimulatory Effects of Low-Power Laser Irradiation on Bone Formation in vitro," SPIE vol. 1984, pp. 281-288.
Panjehpour M et al. "Spectroscopic diagnosis of esophageal cancer: new classification model, improved measurement system." PubMed; Gastrointest Endosc., Jun. 1995; 41 (6):577-81.
Parrish, J.A., "Selective thermal effects with pulsed irradiation from lasers: From organ to organelle," Journal of Investigative Dermatology, vol. 80, No. 6 Supplement, pp. 75s-80s, 1983.
Petrischev et al. "Clinical and Experimental Low-Intense Laser Therapy in Dentistry," SPIE, vol. 1984, pp. 212-214.
Petrischev et al., "Report on Low Intensity Laser Radiation Usage in Dentistry," SPIE vol. 1984, pp. 202-211.
Polanyi, Thomas & Tobias, Irwin, Lasers—A Series of Advances, Edited by A.K. Levine, vol. 2, Marcel Dekker, Inc, N.Y., 1968, pp. 400, 402-403 & 422.
Polla, L. et al., "Melanosomes are a primary target of Q-switched ruby laser irradiation in guinea pig skin," Journal of Investigative Dermatology, vol. 89, No. 3, pp. 281-286, Sep. 1987.
Powell, "Laser Dental Decay Prevention: does it have a future?" SPIE vol. 3192, 1997.
Reed J.T. et al., "Treatment of Periorbital Wrinkles," Washington Inst. of Dermatol. Surg. 23:643-648 (1997).
Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).
Remillard et al., "Diode Laser Illuminators for Night-Vision Applications," SPIE Proceedings vol. 4285:14-22 (2001).
Riggle et al., "Laser Effects on Normal and Tumor Tissue," Laser Applications in Medicine and Biology, vol. 1, M.L. Wolbarsht, editor, Plenum Press, publishers, Ch. 3, pp. 35-65 (1971).
Rohrer, "Evaluating the Safety and Efficacy of a Novel Light Based Hair Removal System," Lasers. Surg. Med. Supp.13:97 (2001).
Rosenfeld, H., et al., "Treatment of Cutaneous and Deep Vascular Lesions with the Nd:YAG Laser," Lasers in Surgery and Medicine, 6:20-23 (1986).
Rotteleur, et al., "Robotized scanning laser handpiece for the treatment of port wine stains and other angiodysplasias," Lasers Surg. Med., 8:283-287 (1998).
Rubach et al., "Histological and Clinical Evaluation of Facial Resurfacing Using a Carbon Dioxide Laser With the Computer Pattern Generator," Arch Otolaryngol Head Neck Surg., 123:929-934 (1997).
Russel et al. "Flash-Lamp-Excited Self-Injection-Seeded Q-Switch Ti:Al2O3 Laser Oscillator," Applied Optics, vol. 35, No. 24 (Aug. 1996).
Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).
Sandford et al., "Thermal Effects During Desensitisation of Teeth with Gallium-Aluminum-Arsenide Lasers," University of Queensland Dental School, Periodontology 15: 25-30 (1994).
Schade, W. et al., "Temperature tuned distributed feedback dye laser with high repetition rate", Applied Optics, vol. 2 9, No. 27, Sep. 20, 1990, pp. 3950-3954.
Schappert et al., "Temperture Tuning of an Organic Dye Laser" Applied Physics Letters 13(4):124-126 (Aug. 15, 1968).

(56) References Cited

OTHER PUBLICATIONS

Schindl, "Does Low Intensity Laser Irradiation Really Cause Cell Damage?" Laser in Surgery and Medicine vol. 22, pp. 105, 2001.
Sheehan-Dare, et al., "Lasers in Dermatology," British Journal of Dermatology, 129:1-8 (1993).
Shimbashi, T. et al., "Ruby laser treatment of pigmented skin lesions," Aesth. Plast. Surg., vol. 19, pp. 225-229, 1995.
Shimizu et al., "Prospect of Relieving Pain Due to Tooth Movement During Orthodontic Treatment Utilizing a GA—Al As Diode Laser," SPIE vol. 1984, pp. 275-280.
Shumilovitch et al., "Influence of Low Intensity Laser Radiation Upon the Microflora of Carious Cavities and Root Canal," SPIE vol. 1984, pp. 215-220.
Shuster, "Acne: The Ashes of a Burnt Out Controversy," Acta Derm. Venereol. Suppl. (Stockh), 120:43-46, 1985.
Sigurdsson et al., "Phototherapy of Acne Vulgaris with Visible Light," Dermatology, 194:256-260, 1997.
Sing, "Electroacupuncture and Laser Stimulation Treatment: Evaluation by Somatosensory Evoked Potential in Conscious Rabbits," Abstract Am-J-Chin-Med. 1997; 25(3-4): 263-71.
Sliney et al., "Safety with Lasers and Other Optical Sources: A Comprehensive Handbook," Plenum Press, pp. 477-480 (1980).
Sokolova et al., "Low-intense Laser Radiation in Complex Treatment of Inflammatory Diseases of Parodontium," SPIE vol. 1984, pp. 234-237.
Spears et al., "Fluorescence of Experimental Atheromatous Plaques with Hematoporphyrin Derivative," J. Clin. Invest, 71:395-399 (1983).
Spotswood, "Novel Use of Fractional Lasers for Scarring Improves Quality of Life for Injured Troops", http://www.usmedicine.com/articles/novel-use-of-fractional-lasers-for-scarring-improves-quality-of-life-for-injured-troops-.html, (Aug. 2012), U.S. Medicine ISSN: 0191-6246. 4 pages.
Stratton, K. et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.
Strauss et al., "Skin Lipids and Acne," Annu. Rev. Med., 26: 27-31, 1975.
Sumian, C.C. et al., "A Preliminary Clinical and Histopathological Study of Laser Skin Resurfacing Using a frequency-Doubled Nd:YAG Laser After Application of Chromofilm®," Journal of Cutaneous Laser Therapy, vol. 1, pp. 159-166, 1999.
Sumian, C.C. et al., "Laser Skin Resurfacing Using a Frequency Doubled Nd:YAG Laser After Topical Application of an Exogenous Chromophore," Lasers in Surgery and Medicine, vol. 25, pp. 43-50, 1999.
Sumian et al., "A new method to improve penetration depth of dyes into the follicular duct: . . . ," J. Am. Acad. Dermotol., 41(2) Part 1:172-175, 1999.
Tarasov, L. V., Laser Physics, Translated from Russion by Ram S. Wadhwa, MIR publishers, Moscow, pp. 178-181, Chapter 2, 1983.
Tarijian, et al., "Fractional abalative laser skin resurfacing: A review", Journal of Cosmetic and Laser Therapy, 13:262-264, ISSN 1476/4172. Informa UK Ltd. Sep. 2011, 3 pages.
Taylor, C.R. et al., "Treatment of tattoos by Q-switched ruby laser," Arch. Dermatol, vol. 126, pp. 893-899, Jul. 1990.
Togatov, V.V. et al., "Electronic discharge module for pump systems of solid-state lasers", Optical Journal, V. 67, n. 4, pp. 92-96 (2000).
Tuchin, V.V., "Laser light scattering in biomedical diagnostics and therapy," Journal of Laser Applications, vol. 5, No. 2-3, pp. 43-60, 1993.
Unger, W.P., Laser hair transplantation III: Computer-assisted laser transplanting. Dermatol Surg. 1995;21:1047-1055.
Van Bruegel, "Power Density and Exposure Time of He—Ne Irradiation Are More Important Than Total Energy Dose in Photo-Biomodulation of Human Fibroblasts in Vitro," Lasers in Surgery and Medicine, vol. 12 pp. 528-537, 1992.
Vasily, et al., "Non-Ablative Fractional Resurfacing of Surgical and Post-Traumatic Scars", Journal of Drugs in Dermatology, 8(11):998-1005, Nov. 2009, 8 pages.
Walsh, "Laser "Curettage": a Critical Analysis," Periodontology 14:4-12, 1993.
Walsh, "The Current Status of Low Level Laser Therapy in Dentistry. Part 1. Soft Tissue Applications," Aust. Dent. J. Aug. 1997;42(4):247-54.
Watanabe, S. et al., "Comparative studies of femtosecond to microsecond laser pulses on selective pigmented cell injury in skin," Photochemistry and Photobiology, vol. 53, No. 6, pp. 757-762, 1991.
Watanabe, S. et al., "The Effect of Pulse Duration on Selective Pigmented Cell Injury by Dye Lasers," The Journal of Investigative Dermatology, 88:523, 1987.
Watson, G. M., MS, "Minimally Invasive Therapies of the Prostate," Minimally Invasive Therapy, 1:231-240 (1992).
Wei Tech Ang et al., "Design of All-Accelerometer Inertial Measurement Unit for Tremor Sensing in Hand-Held Microsurgical Instrument," 2003 IEEE International Conference on Robotics and Automation (vol. 2), Taipei, Taiwan, Sep. 14-19, 2003.
Wei Tech Ang et al., "Kalman Filtering for Real-Time Orientation Tracking of Handheld Microsurgical Instrument," 2004 IEEE/RSJ International Conference on Intelligent Robots and Systems (IROS), Sendai, Japan, Sep. 28-Oct. 2, 2004.
Welch, A.J. et al., "Evaluation of cooling techniques for the protection of the epidermis during HD-yag laser iradiation of the skin," Neodymium-Yag Laser in Medicine and Surgery, Elsevier Science Publishing Co., publisher, pp. 195-204, 1983.
Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.
Wilson, S.W., "Passive Alignment of a Semiconductor Laser to an Optical Fiber," Universirty of Maryland, Master's Thesis (1995).
Winters, B.H. et al., "Photochemical Products in Coumarin Laser Dyes," Appl. Phys. Lett. 25:723-724 (1974).
Yang et al., "Hybrid optoelectronics: A polymer laser pumped by a nitride light emitting diode," Applied Physics Letters 92, Jan. 23, 2008.
Yules, R.B. et al., "The effect of Q-switched ruby laser radiation on dermal tattoo pigment in man," Arch Surg, vol. 95, pp. 179-180, Aug. 1967.
Zapka et al. "Pulse Slicing and Pockels Cell Shutters," J. Phys. E: Sci, Instrum., vol. 15 (1982).
Zayhowski, J.J. et al., "Gain-switched pulsed operation of microchip lasers", Optice Letters, Optical Society of America, US 14:23, Dec. 1, 1989, pp. 1318-1320.
Zeitler, E. et al., "Laser Characteristics that Might be Useful in Biology," Laser Applications in Medicine and Biology, vol. I, M.L. Wolbarsht, editor, Plenum Press, publishers, Chapter 1, pp. 1-18, 1971.
Zonios et al., "Skin Melanin, Hemoglobin, and Light Scattering Properties can be Quantitatively Assessed in Vivo Using Diffuse Reflectance Spectroscopy," Journal of Investigative Dermatology,117:1452-1457 (Dec. 2001).

\* cited by examiner

PICOSECOND LASER APPARATUS AND METHODS FOR TREATING TARGET TISSUES WITH SAME

CROSS REFERENCE TO RELATED APPLICATIONS

This application is a continuation of U.S. patent application Ser. No. 16/784,797, filed Feb. 7, 2020 which is a continuation of U.S. patent application Ser. No. 16/363,597, filed Mar. 25, 2019, now U.S. Pat. No. 10,581,217, which is a continuation of U.S. patent application Ser. No. 15/721,714, filed Sep. 29, 2017, now U.S. Pat. No. 10,305,244, which is a continuation of U.S. patent application Ser. No. 14/394,960, filed Oct. 16, 2014, now U.S. Pat. No. 9,780,518, which is a national phase under 35 U.S.C. § 371 of International Application No. PCT/US2013/032228, filed Mar. 15, 2013, which claims priority to and the benefit of U.S. Provisional Patent Application No. 61/625,961 entitled "Picosecond Laser Apparatus and Methods for Treating Dermal Tissues with Same", filed Apr. 18, 2012, the entire disclosures of which are incorporated herein by reference.

FIELD OF THE INVENTION

The present invention relates to an apparatus and methods for delivering laser energy having a short pulse duration (e.g., less than about 1 nanosecond) and high energy output per pulse (e.g., greater than about 200 millijoules).

SUMMARY OF THE INVENTION

Disclosed herein are subnanosecond pulse duration laser systems, which are useful for a variety of cosmetic and medical treatments. A subnanosecond pulse duration laser apparatus includes: (a) a resonator having a first mirror at one end of said resonator and a second mirror at the opposite end of said resonator, wherein both said first mirror and said second mirror are substantially totally reflective; and (b) a lasing medium, an ultrafast switching element and a polarizing element along the optical axis of said resonator, wherein a first drive circuit is connected to a first end of the ultrafast switching element and a second drive circuit is connected to a second end of the ultrafast switching element, wherein said apparatus generates a modelocked pulse by the first circuit applying a periodic voltage waveform to the first end of the ultrafast switching element and then amplifies the modelocked pulse by the first circuit applying a first constant voltage to the first end of the ultrafast switching element and maintaining an effective reflectivity of the second mirror at substantially 100%, and then extracts the amplified modelocked pulse by the second circuit applying a second constant voltage to the second end of the ultrafast switching element and maintaining an effective reflectivity of the second mirror at substantially 0%.

Subnanosecond pulse duration laser systems that are useful for cosmetic and medical applications provide pulsed laser energy that delivers at least about 100 mJ/pulse and up to about 800 mJ/pulse. An exemplary output energy has about 200 mJ/pulse. Likewise, such subnanosecond laser systems have pulse durations of about 100 picoseconds to less than 1000 ps, and preferably pulse durations of about 200 ps to 600 ps, or about 400-500 ps.

Subnanosecond laser systems are particularly useful in the treatment of skin and skin lesions. For example, tattoo removal requires delivery of subnanosecond laser pulses to the dermis, where photomechanical damage to ink particles facilitates the removal of the tattoo by the subject's immune system. Colored tattoos or heavily shaded tattoos are easily treated by such subnanosecond systems, using fewer treatments to achieve a desired reduction in the visible appearance of the tattoo. Other skin treatments include benign pigmented lesions, where applying subnanosecond pulsed laser energy to benign pigmented lesions decreases the visible appearance of the pigmented lesions. Similar effects are seen in the treatment of vascular lesions, where applying subnanosecond pulsed laser energy to the vascular lesion thereby decreases the visible appearance of the vascular lesions.

In addition to pigmented lesions, scars, wrinkles and striae are also treatable using subnanosecond pulsed laser energy. The laser energy can be used to debulk the scars, and it creates generally areas in the tissue of microdamage from photomechanical effects. This has tissue-inductive effects, resulting in the evening-out of tissue surfaces and the improvement in coloration and texture of the target tissue. In certain aspects of the invention, the subnanosecond pulsed laser energy is modified with a lens, thereby producing a treatment beam having a nonuniform energy cross section characterized by of a plurality of regions of relatively high energy per unit area dispersed within a background region of relatively low energy per unit area. Such systems outputting subnanosecond pulse laser energy in a non-uniform beam deliver sufficient energy to target tissue illuminated by regions of relatively high energy per unit area to heat the so-illuminated portions of the target tissue to a first temperature T1 and wherein the substantially uniform background region of relatively low energy per unit area delivers sufficient energy to target tissue illuminated by the regions of relatively high energy per unit area to heat the so illuminated portions of the target tissue to a second temperature T2, wherein T2 is less than T1.

In other embodiments, the invention provides for wavelength shifted subnanosecond pulse laser, that can be frequency matched to the absorption spectrum of a skin pigment or tattoo ink. A method for shifting the wavelength of a subnanosecond pulse laser apparatus includes maintaining a relatively constant pulse duration by using the pulse as a pump for a laser resonator with a short roundtrip time by including a laser crystal with high absorption coefficient at the wavelength of the short pulse; where the round trip time of the short laser resonator is substantially shorter than the pumping laser pulse duration.

The invention will be more completely understood through the following detailed description, which should be read in conjunction with the attached drawings. Detailed embodiments of the invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the invention in virtually any appropriately detailed embodiment.

DETAILED DESCRIPTION

Lasers are recognized as controllable sources of radiation that is relatively monochromatic and coherent (i.e., has little divergence). Laser energy is applied in an ever-increasing number of areas in diverse fields such as telecommunications, data storage and retrieval, entertainment, research, and many others. In the area of medicine, lasers have proven useful in surgical and cosmetic procedures where a precise beam of high energy radiation causes localized heating and ultimately the destruction of unwanted tissues. Such tissues include, for example, subretinal scar tissue that forms in age-related macular degeneration (AMD) or the constituents of ectatic blood vessels that constitute vascular lesions.

Most of today's aesthetic lasers rely on heat to target tissue and desired results must be balanced against the effects of sustained, elevated temperatures. The principle of selective photothermolysis underlies many conventional medical laser therapies to treat diverse dermatological problems such as leg veins, portwine stain birthmarks, and other ectatic vascular and pigmented lesions. The dermal and epidermal layers containing the targeted structures are exposed to laser energy having a wavelength that is preferentially or selectively absorbed in these structures. This leads to localized heating to a temperature (e.g., to about 70 degrees C.) that denatures constituent proteins or disperses pigment particles. The fluence, or energy per unit area, used to accomplish this denaturation or dispersion is generally based on the amount required to achieve the desired targeted tissue temperature, before a significant portion of the absorbed laser energy is lost to diffusion. The fluence must, however, be limited to avoid denaturing tissues surrounding the targeted area.

Fluence, however, is not the only consideration governing the suitability of laser energy for particular applications. The pulse duration and pulse intensity, for example, can impact the degree to which laser energy diffuses into surrounding tissues during the pulse and/or causes undesired, localized vaporization. In terms of the pulse duration of the laser energy used, conventional approaches have focused on maintaining this value below the thermal relaxation time of the targeted structures, in order to achieve optimum heating. For the small vessels contained in portwine stain birthmarks, for example, thermal relaxation times and hence the corresponding pulse durations of the treating radiation are often on the order of hundreds of microseconds to several milliseconds.

Cynosure's PicoSure™ brand laser system is the first aesthetic laser to utilize picosecond technology which delivers laser energy at speeds measured in trillionth of seconds ($10^{-12}$). PicoSure systems deliver both heat and mechanical stress to shatter the target from within before any substantial thermal energy can disperse to surrounding tissue. Clinical results show a higher percentage of clearance achieved in fewer treatments. PicoSure systems, employing Pressure Wave™ technology, is useful for multiple aesthetic indications such as pigmented lesions and multi-colored tattoo removal as well as dermal rejuvenation.

An exemplary PicoSure™ brand picosecond laser apparatus is detailed in our U.S. Pat. Nos. 7,586,957 and 7,929,579, incorporated herein by reference. Such a laser apparatus provides for extremely short pulse durations, resulting in a different approach to treating dermal conditions than traditional photothermal treatments. Laser pulses having durations below the acoustic transit time of a sound wave through targeted particles are capable of generating photomechanical effects through pressure built up in the target particles. Photomechanical processes can provide commercially significant opportunities, particularly in the area of treating skin pigmentations. Coupled with high energy output, such lasers described above are particularly suitable for the following exemplary applications. Table 1. provides fluence values for particular spot sizes, for a subnanosecond pulse laser outputting about 200 mJ/pulse.

TABLE 1

| PicoSure Fluence | |
|---|---|
| Spot size | J/cm^2 |
| 2 | 6.369 |
| 2.5 | 4.076 |
| 3 | 2.831 |
| 3.5 | 2.080 |
| 4 | 1.592 |
| 4.5 | 1.258 |
| 5 | 1.019 |
| 5.5 | 0.842 |
| 6 | 0.708 |
| 8 | 0.398 |
| 10 | 0.255 |

A. Tattoo Removal

The incidence of tattoos in the U.S. and other populations, for example, continues at a significant pace. Because tattoo pigment particles of about 1 micron in diameter or less may be cleared from the body via ordinary immune system processes, stable tattoos are likely composed of pigment particles having diameters on the order of 1-10 microns or more. The acoustic transit time of a sound wave in a particle of tattoo pigment is calculated by dividing the radius of the particle by the speed of sound in the particle. As the speed of sound in tattoo pigment, as well as many solid media is approximately 3000 meters/second, the acoustic transit time across such particles, and consequently the laser pulse duration required to achieve their photomechanical destruction of the tattoo pigment is as low as hundreds of picoseconds.

In addition to such short pulse durations, high energy laser pulses are needed for significant disruption of tattoo pigment particles. Given that most tattoos are on the order of multiple centimeters in size, the ideal laser for tattoo removal should ideally employ a beam having a relatively large spot size. Fluences of several joules per square centimeter and treatment spot sizes of a few millimeters in diameter translate to a desired laser output with several hundred millijoules (mJ) per pulse or more, and are suitable for tattoo removal.

An exemplary sub-nanosecond tattoo removal laser apparatus as described in our U.S. Pat. Nos. 7,586,957 and 7,929,579 and as described herein is used to generate pulsed laser energy having a subnanosecond pulse duration of about 100-950 picoseconds, preferably with an energy delivery of about 200-750 mJ/pulse. Such exemplary subnanosecond laser apparatus includes a resonator with two substantially totally reflective mirrors at opposite ends of its optical axis. An alexandrite crystal lasing medium, a polarizer, and a Pockels cell are positioned along this optical axis. An optical flashlamp is also included for pumping the alexandrite lasing medium, which generates laser energy having a wavelength in the range of about 700-950 nm.

The pulsed laser energy described above is generated by pumping the lasing medium and first establishing a modelocked pulse oscillating in the resonator. In the modelocked pulse operating mode, a time-dependent voltage waveform, as described herein, is applied to the Pockels cell. This waveform results from the sum of a constant baseline voltage and a time-dependent differential voltage. The baseline voltage is in the range of 1000-1500 volts (representing 40-60% of the Pockels cell quarter wave voltage, or 2500 volts) and is negatively offset or modulated by the time-dependent differential voltage, having an amplitude in the range of 250-750 volts (representing 10%-30% of the Pockels cell quarter wave voltage). The period of the resulting voltage waveform is in the range from 5-10 ns and is equal to the round trip time of the oscillating laser energy in the resonator. The voltage applied to the Pockels cell is thus modulated at a frequency in the range from 100-200 MHz.

Subsequently, the modelocked pulse established as described above is amplified by discharging the Pockets cell to essentially 0 volts. Oscillating laser energy is reflected between the mirrors at each end of the resonator, with essentially no losses. This laser energy therefore rapidly increases in amplitude by extracting energy previously pumped and stored in the alexandrite crystal during modelocking. When the laser energy has reached the desired energy level as indicated above, it is extracted from the resonator by applying the quarter wave voltage of 2500 volts to the Pockels cell.

The switching electronics used to operate the laser in modelocked pulse and amplification modes, and finally to extract the amplified pulse as discussed above, comprise five MOSFET switches, two high speed diodes, and three voltage sources having voltages $V1$ in the range of +1000 to +1500 volts, $V2$ in the range of +250 to +750 volts, and $V3$ in the range of −1000 to −1500 volts. The switches, diodes, and voltage sources are configured as shown above.

Laser energy having the pulse duration and energy as described above is applied to a patient undergoing treatment for the removal of a tattoo. This laser energy is applied over the course of a 30-minute treatment session to all areas of the skin having undesired tattoo pigment particles. Photomechanical disruption of these particles is effected using the short pulse duration (below the transit time of a sound wave through the targeted tattoo pigment particles), together with a fluence in the range of 2-4 $J/cm^2$. This fluence is achieved in the above device with a laser energy spot diameter of about 5 mm.

Most if not all of the undesired tattoo pigment particles are effectively photomechanically disrupted, destabilized, and/or broken apart using one or two treatments. As a result, the disrupted particles are cleared from the body via normal physiological processes, such as the immune response. The tattoo is thus eventually cleared from the skin with no remaining visible signs. Such subnanosecond laser devices are particularly well suited for removal of tattoos having colored inks, colors being far more recalcitrant to treatment with traditional laser treatments than black inks. Likewise, tattoos having heavy coloration or shading are more amenable to treatment using subnanosecond laser systems. Similarly, subnanosecond lasers provide for tattoo removal with fewer treatments than compared to traditional laser systems.

B. Benign Pigmented Lesions

Numerous types of benign pigmented lesions of the skin, connective tissue, mucosal tissue and vasculature are treatable using the subnanosecond laser systems described herein.

Nevi are a broad category of generally well circumscribed and chronic lesions of the skin that can be congenital or develop later in life. Vascular nevi such as hemangioma, are derived from structures of the blood vessels. Epidermal nevi such as seborrheic keratoses are derived from keratinocytes. Connective tissue nevi are derived from connective tissues. Melanocytic nevi such as nevomelanocytic nevi are pigmented lesions that morphologically can be flat macules or raised papules, and are characterized by clusters of melanocytes. In addition to the above, dermal melanocytoma (blue nevi), acral nevi, nevus spilus (also known as speckled lentiginous nevus), nevus of Ota/Ito and Becker's nevus are all exemplary and non-limiting nevi that are suitable for treatment using the above laser apparatus.

Lentigines are similarly treatable. These are pigmented spots on the skin typically small and with a clearly-defined edge, surrounded by normal-appearing skin. These are benign melanocytic hyperplasias that are linear rather than raised, with the melanocytes generally restricted to the cell layer directly above the basement membrane of the epidermis. Lentigines also appear in mucosal tissues. Lentigines are distinguished from ephelids (freckles) based on melanocyte proliferation, where lentigines display an increased number of melanocytes but ephelids have normal numbers of melanocytes that overexpress melanin.

Other forms of congenital dermal pigmentation are equally suitable to treatment using the above laser apparatus, usually being larger areas requiring larger laser spot sizes. For example, café au lait macules, congenital dermal melanocytosis, and dermal melanocytosis are all exemplary types of benign, flat, pigmented birthmarks, generally with wavy borders and irregular shapes. Other exemplary pigmented lesions develop as one ages, or due to hormonal changes, infection or treatment with pharmaceutical agents. For example, melasma a/k/a chloasma faciei (colloquially "the mask of pregnancy") is a tan or dark skin discoloration. Postinflammatory hyperpigmentation (also known as postinflammatory hypermelanosis) can result from natural or iatrogenic inflammatory conditions, and are commonly caused by increased epidermal pigmentation. This can occur through increased melanocyte activity or by dermal melanosis from melanocyte damage with melanin migration from the epidermis into the dermis. Drug-induced pigmentation of the skin may occur as a consequence of drug administration, related to deposition of the drug in the tissues. Minocycline is known for this effect. Pigmented lesions aren't confined to the dermal tissues. Ochronosis is a pigmented lesion caused by the accumulation of homogentisic acid in connective tissues. In addition, melanonychia is aberrant pigmentation of the normal nail plate. These exemplary conditions are all suitable to treatments using the above described laser systems.

To treat the above conditions, it is generally accepted that destruction of melanosomes is pulse-width-dependent. Using traditional laser systems, pulse durations of between 40 nanoseconds and 750 nanoseconds have been shown to be effective, but longer pulse durations (eg, 400 microseconds) do not appreciably damage the melanosomes. Likewise, Q-switched Nd:YAG laser systems have shown immediate skin whitening with threshold energy exposures generating fluence values of 0.11, 0.2, and 1 $J/cm^2$ respectively at 355, 532, and 1064 nm wavelengths.

Melanin has a broad absorption spectrum, and lasers emitting at wavelengths of about 500-1100 nm provide for good skin penetration and selective melanosome absorption without undue hemoglobin absorption. Exemplary lasers include 510-nm pulsed dye, 532-nm frequency-doubled Nd:YAG, 694-nm ruby, 755-nm alexandrite, and near-infrared Nd:YAG lasers emitting at 1064 nm. Other lasers have been used successfully to treat pigmented lesions, including argon, krypton, copper, carbon dioxide, and Er:YAG lasers, but with these systems there is a trade-off between pigment destruction and collateral damage to other chromophores and tissues.

An exemplary subnanosecond laser system for treating pigmented lesions is described by the above apparatus generating pulsed laser energy having a pulse duration of about 100-950 picoseconds with an energy output of about 200-750 mJ/pulse. Laser energy having a wavelength in the range of 700-950 nm provides excellent specificity for melanin. Photomechanical disruption is effected using the short pulse duration (below the transit time of a sound wave through the targeted pigment particles), together with a fluence in the range of 2-4 J/cm$^2$. This fluence is achieved with a laser energy spot diameter of about 5 mm, which can be changed according to the area of the target. Treatment times will vary with the degree of pigmentation and the shapes of the targets. In addition to decreasing the visible appearance of pigmented lesions, photomechanical microdamage to target tissues caused by subnanosecond pulses promotes a healing response that can decrease the size and shape of the lesion.

C. Vascular Lesions

Vascular lesions refer to a broad category of pigmented malformations, generally congenital, that are due to localized defects of vascular morphogenesis. These include capillary, venous, arteriovenous, and lymphatic malformations as well as lesions involving only the skin and subcutaneous tissues. Exemplary non-limiting examples include capillary vascular malformation, telangiectasis, cherry angioma, angiofibroma, dyschromia, port wine stain birthmarks, strawberry hemangiomas, rosacea, pyogenic granuloma and other vascular malformations.

The targeted chromophore for vascular lesions is intravascular oxyhemoglobin, with maximal light absorption occurring in the range of yellow and green light, i.e., at 418, 542, and 577 nm and in the near-infrared spectrum. Traditional approaches to treating vascular lesions involved pulsed dye lasers, typically operating at wavelengths such as 585-nm or 595-nm, frequency-doubled Nd:YAG lasers at wavelengths of 532 nm, and infrared lasers such as alexandrite or diode lasers having wavelengths of 1064 nm. Histologically, the targets of treatment are postcapillary venules, capillaries, or arterioles, generally at depths range from 200 to 300 μm. Accordingly, a deeper penetration of the laser beam is desirable, particularly where heating of the surface skin can lead to excessive scarring. Typical treatment parameters involve fluences of 8 to 10 J/cm$^2$, and a 5-10 mm spot size.

An exemplary system to treat vascular lesions is described by an apparatus generating pulsed laser energy having a pulse duration of about 100-950 ps with energies of about 200-750 mJ/pulse. Laser energy having a wavelength in the range of 500-600 nm provides excellent specificity for oxyhemoglobin. Photomechanical disruption is effected using the short pulse duration (below the transit time of a sound wave through the targeted pigment particles), together with a fluence in the range of 7-10 j/cm$^2$. This fluence is achieved with a laser energy spot diameter of about 5 mm, which can be changed according to the area of the target. Treatment times will vary with the degree of pigmentation and the shapes of the targets.

D. Scar Tissue

Various types of scarring are treatable using lasers. Exemplary non-limiting types include hypertrophic scars, keloids and atrophic scars. Hypertrophic scars are cutaneous deposits of excessive amounts of collagen. These give rise to a raised scar, and are commonly seen at prior injury sites particularly where the trauma involves deep layers of the dermis, i.e., cuts and burns, body piercings, or from pimples. Hypertrophic scars commonly contain nerve endings are vascularized, and usually do not extend far beyond the boundary of the original injury site.

Similarly, a keloid is a type of scar resulting from injury, that is composed mainly of either type III or type I collagen. Keloids result from an overgrowth of collagen at the site of an injury (type III), which is eventually replaced with type 1 collagen, resulting in raised, puffy appearing firm, rubbery lesions or shiny, fibrous nodules, which can affect movement of the skin. Coloration can vary from pink to darker brown.

Atrophic scarring generally refers to depressions in the tissue, such as those seen resulting from Acne vulgaris infection. These "ice pick" scars can also be caused by atrophia maculosa varioliformis cutis (AMVC), which is a rare condition involving spontaneous depressed scarring, on the cheeks, temple area and forehead.

Laser treatments are suitable for hypertrophic and atrophic scars, and keloids, and common approaches have employed pulsed dye lasers in such treatments. In raised scars, this type of therapy appears to decrease scar tissue volume through suppression of fibroblast proliferation and collagen expression, as well as induction of apoptotic mechanisms. Combination treatment with corticosteroids and cytotoxic agents such as fluorouracil can also improve outcome. In atrophic scars, treatments can even out tissue depths.

Striae (stretch marks) are a form of scarring caused by tearing of the dermis. They result from excess levels of glucocorticoid hormones, which prevent dermal fibroblasts from expressing collagen and elastin. This leads to dermal and epidermal tearing. Generally, 585-nm pulsed dye laser treatments show subjective improvement, but can increase pigmentation in darker skinned individuals with repeated treatments. Fractional laser resurfacing using scattered pulses of light has been attempted. This targets small regions of the scar at one time, requiring several treatments. The mechanism is believed to be the creation of microscopic trauma to the scar, which results in new collagen formation and epithelial regeneration. Similar results can be achieved, albeit to the total scar, through the use of modified laser beams as described in our U.S. Pat. No. 7,856,985, detailing the use of non-uniform beam radiation to create within the beam area, discrete microtrauma sites against a background of tissue inducing laser radiation.

An exemplary system for treating scars is described by the above apparatus generating pulsed laser energy having a pulse duration of about 100-950 ps with energies of about 200-750 mJ/pulse. Laser energy having a wavelength in the range of 500-1100 nm provides excellent specificity for collagen. Photomechanical disruption of the scar tissue is effected using the short pulse duration (below the transit time of a sound wave through the targeted tissue), together with a fluence in the range of 2-4 J/cm$^2$. This fluence is achieved with a laser energy spot diameter of about 5 mm, which can be changed according to the area of the target. Treatment times will vary with the degree of scarring and the shapes of the targets. The photomicrodamage from subnanosecond pulses can debulk the scar, resolve coloration differences between it and healthy tissues, and promotes tissue healing responses which have the effect of softening the scar. Modifying the output beam as described in U.S. Pat. No. 7,856,985 provides a particularly useful approach to reducing scar appearance and inducing epithelial restoration within the scar.

E. Dermal Rejuvenation

A non-uniform output beam is delivered to tissue from a source of light as described in our patent application U.S. Ser. Nos. 11/347,672; 12/635,295; 12/947,310, and PCT/US10/026432. The non-uniform beam is characterized by a cross-section corresponding to an array of relatively small, relatively high-intensity, spaced-apart central regions superimposed on a relatively large, and relatively low-intensity background region. Operatively, this produces within the area of the beam, relatively hotter regions and relatively cooler regions. This non-uniform beam provides for unique physiological effects as compared to standard uniform output laser beams that demonstrate relative uniform energy output across the planar surface of the beam. Such effects are related to the fluence and duration of the light pulse, and include various quantifiable physiological effects. Exemplary temperature dependent effects include but are not limited to parakeratosis, perivascular mononuclear infiltration, keratinocyte necrosis, collagen denaturation, and procollagen expression in dermal cells. Other cellular markers (e.g., nucleic acids and proteins) are useful in detecting more subtle responses of skin to less aggressive treatments.

Various combinations of wavelength, power, spot size, treatment duration and recovery intervals are possible, and the particular combination is selected based on the desired therapeutic effect. For example, in treating age spots and pigmentation a device wavelength is chosen to be preferentially absorbed by melanin (between 400 nm and 1400 nm, and more preferably 500 nm to 1100 nm). Accordingly, an exemplary device for such purposes has a wavelength of about 750 nm, a pulse duration of about 500 to 900 ps and an overall treatment area of 1 cm that is output as a non-uniform beam characterized by a cross-section corresponding to an array of relatively small, relatively high intensity, spaced-apart central regions superimposed on a relatively large, relatively low intensity background region. If such exemplary device has about 0.2 J of energy delivered into the treatment area, or about 0.2 J/cm$^2$ average fluence. Using a lens that renders the output beam non-uniform, delivering relatively high intensity spaced-apart central regions at 1 mm center-to-center distances surrounded by low intensity background regions, in such device, there are about 115 discrete subzones (e.g., combined areas of relatively high and relatively low intensity) per square centimeter in that arrangement, which results in about 1.73 mJ delivered to each subzone. Within each subzone, if the high intensity spaced-apart central region is about 120 μm in diameter and approximately 80% of the energy is delivered into the high intensity spaced-apart central regions, then the fluence within each high intensity region is approximately 12.2 J/cm$^2$. That fluence value in the device is comparable to the treatment fluence delivered by high-powered Alexandrite uniform spot lasers having pulse durations of about 50 ns, which are the systems commonly used to treat uneven skin pigmentation in clinical settings by medically trained professionals. Unlike uniform-beam devices, using the non-uniform beam technology for any individual treatment session, only a relatively small percentage of the irradiated skin surface is actually treated with high intensity light, and thereby only a subpopulation of melanocytes receive a cellular disruptive dose of thermal energy, leading to a relatively smaller percentage of melanocyte damage per treatment area compared to uniform beam treatments. This advantageously reduces any sharp boundaries between treated and untreated skin, thereby reducing the need for special operator skills and techniques.

Good cosmetic effects can be produced by such non-uniform irradiation of tissues, due to differential effects occurring in both the relatively high intensity spaced-apart central regions of the beam and in the relatively low intensity background region. By way of illustration, within the spaced-apart central regions it is possible to cause relatively localized heating of tissues therein to a temperature $T_1$ sufficient to heat up the melanocytes to a temperature sufficient to disrupt cellular processes (e.g., about 45 degrees C. or higher), impair their function and decrease their pigment output. Simultaneously during the treatment, within the low intensity background regions at a lower relative temperature $T_2$ (e.g., less than 45 degrees C. to about 35 degrees C.), cellular growth and collagen production is induced without causing undesirable thermal effects to the treated tissue within the lower energy regions. The result of such treatment is an improvement to both skin texture and coloration. Other differential effects on tissues can be realized as well. By way of further example, temperatures at about 70 degrees C. can serve to denature collagen, so within the spaced-apart central regions it is possible to cause relatively localized heating of tissues therein to a temperature $T_1$ sufficient to remodel collagen structures, while simultaneously within the low intensity background regions at a lower relative temperature $T_2$, collagen production is induced without causing undesirable thermal effects to the treated tissue within the background regions.

Likewise, by decreasing the amount of energy delivered by the beam it is possible to select for specific thermal effects on tissues. For example, in our U.S. Pat. No. 7,856,985 we disclose collagen remodeling at temperatures where $T_1$ is approximately 70 degrees C. or greater while the irradiated tissues in the cooler regions of the beam (e.g., at temperature $T_2$) are not substantially adversely affected. The device used generating a non-uniform beam output, permits more selective application with less collateral tissue damage. However, for reducing age spots and evening skin pigmentation, melanocyte cell membrane damage with consequent cellular disruption is achieved at lower $T_1$ temperatures of approximately 45-50 degrees C. (unless such heating is quite transient). Higher temperatures are suitable, and cause permanent disruption of melanocytes, but above 50 degrees C. more extensive thermal effects are seen in the tissue, that must be evaluated against therapeutic benefits. Below the temperature threshold for causing cellular damage and disruption, positive effects on skin tone are seen. At a $T_1$ temperature of less than about 50 degrees C., cells are not substantially damaged but are still induced to generate a healing response, and express elastin, procollagen, keratin and other markers for dermal rejuvenation. So a device generating regions capable of elevating tissue temperatures to a $T_1$ of about 45 degrees C. against a background $T_2$ of about 37 degrees.

The overall effect of treatments on skin tone, wrinkling and pigmentation provide the best indication of therapeutic efficacy, but such treatments also leave histological effects that can be discerned. At higher energies, thermal damage is easy to detect. For more moderate energies, microthermal damage can produce effects that are seen with magnification although erythema provides a good marker for microthermal injury and it does not require microscopic examination of tissues from the treatment site. Generally, in the absence of any visually observable erythema, the cellular effects will be more subtle, or may take longer to manifest themselves or may require multiple treatments before visual improvement of the skin is seen. At lower output energies, shorter pulse durations, and longer intervals between treatments, it is advantageous to use more sensitive techniques to assay for cellular changes. Certain techniques provide for quantitative analysis, which are correlated to describe a dose-response relationship for the non-uniform beam, as it is used in dermal rejuvenation applications. Such techniques include but are not limited to RT-PCR and/or real-time PCR, either of which permits quantitative measurements of gene transcription, useful to determine how expression of a particular marker gene in the treated tissues changes over time. In addition to nucleic acid-based techniques, quantitative proteomics can determine the relative protein abundance between samples. Such techniques include 2-D electrophoresis, and mass spectroscopy (MS) such as MALDI-MS/MS and ESI-MS/MS. Current MS methods include but are not limited to: isotope-coded affinity tags (ICAT); isobaric labeling; tandem mass tags (TMT); isobaric tags for relative and absolute quantitation (iTRAQ); and metal-coded tags (Me-CATs). MeCAT can be used in combination with element mass spectrometry ICP-MS allowing first-time absolute quantification of the metal bound by MeCAT reagent to a protein or biomolecule, enabling detection of the absolute amount of protein down to attomolar range.

An exemplary system for dermal rejuvenation is described by the above apparatus generating pulsed laser energy having a pulse duration of about 100-950 ps with energies about 200-750 mJ/pulse. Laser energy having a wavelength in the range of 500-1100 nm provides excellent specificity for collagen. Photomechanical disruption of the target tissue is effected using the short pulse duration (below the transit time of a sound wave through the targeted tissue), together with a fluence in the range of 2-4 J/cm$^2$. This fluence is achieved with a laser energy spot diameter of about 5 mm, which can be changed according to the area of the target. Treatment times will vary according to the desired effects. Modifying the output beam as described in U.S. Pat. No. 7,856,985 provides a particularly useful approach to rejuvenating tissue and inducing collagen and epithelial cell restoration within the tissue.

F. Frequency Shifting

The subnanosecond laser systems may include a frequency shifting apparatus, which can be matched to the absorption spectrum of endogenous skin pigmentation or exogenous tattoo pigments to be targeted. Such a system comprises a rare earth doped laser gain crystal for example Nd:YVO4, and a frequency doubling crystal for example KTP. Rare earth doped laser crystals that generate a polarized laser beam like Nd:YVO4 are preferred. Crystals like Nd:YAG or Nd doped glasses can be used with an additional polarizing element in the resonator. The input side of the Nd:YVO4 crystal is AR coated for the alexandrite wavelength and HR coated for 1064 nm. The output side of the crystal is HR coated for the alexandrite wavelength and has approximately 20 to 70% reflectivity at 1064 nm. The Nd:YVO4 crystal length is chosen so that it absorbs most (greater than 90%) of the alexandrite laser pulse in the two passes through the crystal. For Nd doping in the range 1 to 3% the Nd:YVO4 crystal can be chosen to be around 3 mm long. There are no other optical elements in the resonator and the resonator length is equal to the crystal length 3 mm. That means the resonator round-trip time is around 36 ps—this is substantially less than the pulse duration of the alexandrite pumping pulse (around 500 to 800 ps). The 1064 nm pulse generated in the very short round trip time Nd:YVO4 resonator will be slightly longer than the pumping alexandrite pulse and it will be shorter than 1000 ps. The quantum defect will account for a 30% pulse energy loss and another 15% of the energy is likely to be lost due to coatings, crystal and geometry imperfection for an overall energy conversion efficiency of around 50 to 60%. That means a 100 mJ pulse energy can be expected at 1064 nm. Conservatively it is estimated that the second harmonic conversion in the KTP crystal will be around 50% and a 50 mJ pulse energy can be expected at 532 nm. The red tattoo pigments have high absorption at 532 nm. A 50 mJ 532 nm pulse with a pulse duration less than 1000 ps is expected to be effective at disrupting red tattoo granules.

When the Nd:YAG crystal or Nd doped glasses are used in the short resonator an extra polarizing element has to be used to generate a polarized 1064 nm pulse. The cross-section depicts a short Nd:YAG resonator consisting of two identically shaped crystals with one face cut at an angle that is AR coated for the alexandrite wavelength and polarized coating for 1064 nm (high p transmission). The flat faces of the two Nd:YAG crystals have different coatings-one is AR coated at 755 nm and HR coated at 1064 nm and the other is HR coated for 755 nm and has an output coupler reflectivity around 50 to 80% for 1064 nm. The higher output coupler reflectivity for the Nd:YAG crystal compared to the Nd:YVO4 crystal is due to the lower gain cross-section in Nd:YAG.

Generating a short 1064 nm pulse depends on two factors. One is the pulse duration of the pumping alexandrite pulse. Shorter pumping pulses will lead to shorter generated pulses at 1064 nm. The second factor is the 1064 nm resonator round trip time that is determined by the length of the Nd doped crystal. Shorter crystals lead to shorter roundtrip time, however the crystal has to be sufficiently long to absorb greater than 90% of the alexandrite energy. For example, an 8 mm long Nd:YAG resonator would have a 97 ps round trip time. That round trip time is longer than the round trip time that can be achieved with a Nd:YVO4 resonator, but still it is much shorter than the pumping Alexandrite laser pulse duration. One possible way to shorten the crystal length is to tune the alexandrite laser in the range 750 to 760 nm for maximum absorption in the Nd doped crystal and use the minimum possible crystal length. In addition, tuning the alexandrite laser in the range 750 to 757 nm allows for the alexandrite wavelength to be set to avoid the excited state absorption bands in the Nd ion as described by Kliewer and Powell, IEEE Journal of Quantum Electronics vol. 25, page 1850-1854, 1989.

The invention claimed is:

1. A method of treating a target tissue comprising one or more scars, the method comprising:
generating, using a laser source, an output beam having a subnanosecond pulse duration;
modifying the output beam, using an optical system, to provide a photomechanically disruptive treatment beam;
directing the photomechanically disruptive treatment beam to the one or more scars, wherein the one or more scars is one or more atrophic scars;
photomechanically disrupting the one or more scars; and
decreasing visible appearance of the one or more scars in response to the treatment beam.

2. The method of claim 1 wherein decreasing visible appearance of the one or more scars comprises decreasing scar tissue volume.

3. The method of claim 2 wherein decreasing scar tissue volume comprises suppressing fibroblast proliferation.

4. The method of claim 2 wherein decreasing scar tissue volume comprises suppressing collagen expression.

5. The method of claim 1 wherein the one or more scars are in a treatment region, further comprising applying a corticosteroid to the treatment region.

6. The method of claim 1 wherein the one or more scars are in a treatment region, further comprising applying a cytotoxic agent to the treatment region.

7. The method of claim 1 wherein the one or more scars are in a treatment region, wherein decreasing visible appearance of the one or more scars comprises evening out tissue depth in treatment region.

8. The method of claim 1, wherein the treatment beam has a non-uniform profile.

9. The method of claim 8, wherein the non-uniform profile comprises a first energy distribution and a second energy distribution.

10. The method of claim 8, wherein the non-uniform profile comprises a plurality of regions of relatively high energy per unit area dispersed within a substantially uniform background region of relatively low energy per unit area.

11. The method of claim 9 further comprising increasing temperature of a first region of scar tissue to a first temperature T1 and increasing or maintaining temperature of a second region of scar tissue to a second temperature T2 using the non-uniform distribution of the treatment beam.

12. The method of claim 11 wherein T1 ranges from about 45 degrees Celsius to about 50 degrees Celsius.

13. The method of claim 1 wherein the treatment beam has a non-uniform profile comprising a plurality of regions of relatively high energy per unit area dispersed within a substantially uniform background region of relatively low energy per unit area.

14. The method of claim 13, wherein the target tissue comprising one or more scars comprises a dermal layer and an epidermal layer further comprising increasing temperature of at least one of the dermal layer and the epidermal of the one or more scars to a first temperature T1 and increasing or maintaining temperature of a second region of scar tissue to a second temperature T2 using the non-uniform distribution of the treatment beam.

15. The method of claim 14 wherein T1 ranges from about 45 degrees Celsius to about 50 degrees Celsius.

16. The method of claim 14 wherein T1 is approximately 70 degrees Celsius or greater.

17. A method of treating a target tissue comprising one or more scars, the method comprising:
  generating, using a laser source, an output beam having a subnanosecond pulse duration;
  modifying the output beam, using an optical system, to provide a photomechanically disruptive treatment beam;
  directing the photomechanically disruptive treatment beam to the one or more scars, wherein the one or more scars is one or more hypertrophic scars;
  photomechanically disrupting the one or more scars; and
  decreasing visible appearance of the one or more scars in response to the treatment beam.

18. The method of claim 17 wherein decreasing visible appearance of the one or more scars comprises decreasing scar tissue volume.

19. The method of claim 18 wherein decreasing scar tissue volume comprises suppressing fibroblast proliferation.

20. The method of claim 18 wherein decreasing scar tissue volume comprises suppressing collagen expression.

21. The method of claim 17 wherein the one or more scars are in a treatment region, further comprising applying a corticosteroid to the treatment region.

22. The method of claim 17 wherein the one or more scars are in a treatment region, further comprising applying a cytotoxic agent to the treatment region.

23. The method of claim 17 wherein the one or more scars are in a treatment region, wherein decreasing visible appearance of the one or more scars comprises evening out tissue depth in treatment region.

24. The method of claim 17, wherein the treatment beam has a non-uniform profile.

25. The method of claim 24, wherein the non-uniform profile comprises a first energy distribution and a second energy distribution.

26. The method of claim 24, wherein the non-uniform profile comprises a plurality of regions of relatively high energy per unit area dispersed within a substantially uniform background region of relatively low energy per unit area.

27. The method of claim 25 further comprising increasing temperature of a first region of scar tissue to a first temperature T1 and increasing or maintaining temperature of a second region of scar tissue to a second temperature T2 using the non-uniform distribution of the treatment beam.

28. The method of claim 27 wherein T1 ranges from about 45 degrees Celsius to about 50 degrees Celsius.

29. The method of claim 17 wherein the treatment beam has a non-uniform profile comprising a plurality of regions of relatively high energy per unit area dispersed within a substantially uniform background region of relatively low energy per unit area.

30. The method of claim 29, wherein the target tissue comprising one or more scars comprises a dermal layer and an epidermal layer further comprising increasing temperature of at least one of the dermal layer and the epidermal of the one or more scars to a first temperature T1 and increasing or maintaining temperature of a second region of scar tissue to a second temperature T2 using the non-uniform distribution of the treatment beam.

31. The method of claim 30 wherein T1 ranges from about 45 degrees Celsius to about 50 degrees Celsius.

32. The method of claim 30 wherein T1 is approximately 70 degrees Celsius or greater.

* * * * *